(12) United States Patent
Christakis et al.

(10) Patent No.: US 12,048,822 B2
(45) Date of Patent: *Jul. 30, 2024

(54) DELIVERY DEVICES AND METHODS

(71) Applicant: Boston Scientific Scimed, Inc., Maple Grove, MN (US)

(72) Inventors: Laura Christakis, Framingham, MA (US); Ashleigh Peterson, St. Albans, VT (US); Jeffrey Bean, Fitchburg, MA (US); Claude Clerc, Marlborough, MA (US); Andrew Pic, Wilmington, DE (US); Gerald Fredrickson, Westford, MA (US); Stan Gilbert, Litchfield, NH (US); Amanda Smith, Brookline, MA (US); Jose Vega, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 18 days.

This patent is subject to a terminal disclaimer.

(21) Appl. No.: 17/884,150

(22) Filed: Aug. 9, 2022

(65) Prior Publication Data

US 2022/0379102 A1 Dec. 1, 2022

Related U.S. Application Data

(63) Continuation of application No. 16/560,664, filed on Sep. 4, 2019, now Pat. No. 11,433,223, which is a
(Continued)

(51) Int. Cl.
*A61M 31/00* (2006.01)
*A61B 17/00* (2006.01)
(Continued)

(52) U.S. Cl.
CPC ....... *A61M 31/002* (2013.01); *A61B 17/0057* (2013.01); *A61M 1/304* (2014.02); *A61M 11/007* (2014.02); *A61M 2205/332* (2013.01)

(58) Field of Classification Search
CPC .. A61M 31/002; A61M 1/304; A61M 11/007; A61M 2205/332; A61M 15/0008;
(Continued)

(56) References Cited

U.S. PATENT DOCUMENTS 471,854 A 3/1892 Howard
881,238 A 3/1908 Hasbrouck
(Continued)

FOREIGN PATENT DOCUMENTS

CN 101401956 B 11/2012
DE 60215438 T2 8/2007
(Continued)

OTHER PUBLICATIONS

Bridevaux, Pierre-Olivier, et al. "Short-term safety of thoracoscopic talc pleurodesis for recurrent primary spontaneous pneumothorax: a prospective European multicentre study." European Respiratory Journal 38.4 (2011): 770-773.
(Continued)

*Primary Examiner* — Theodore J Stigell
(74) *Attorney, Agent, or Firm* — Bookoff McAndrews, PLLC

(57) ABSTRACT

Implementations of a delivery device and method are disclosed. One implementation is a delivery device comprising a flow chamber with an inlet port for receiving a fluid flow in the flow chamber, and an outlet port for exiting a material from the flow chamber. The flow chamber may include a formation portion in which a suspension of the material is formed, and a collection portion that directs the suspension toward and/or into the outlet port. An amount of the material
(Continued)

may collect in the collection portion adjacent the outlet port. The device may further comprise an insertion port for permitting insertion of the material in the flow chamber, and/or a pusher operable to move the amount of material through the outlet port. Related devices and methods also are disclosed.

19 Claims, 14 Drawing Sheets

Related U.S. Application Data continuation of application No. 15/637,743, filed on Jun. 29, 2017, now Pat. No. 10,441,761.

(60) Provisional application No. 62/357,425, filed on Jul. 1, 2016.

(51) Int. Cl.
*A61M 1/30* (2006.01)
*A61M 11/00* (2006.01)

(58) Field of Classification Search
CPC .. A61M 11/02; A61M 2206/16; A61M 13/00; A61M 2202/064; A61M 2206/11; A61B 17/0057; A61B 2017/00676
See application file for complete search history.

(56) References Cited

U.S. PATENT DOCUMENTS

| | | | |
|---|---|---|---|
| 1,145,520 A | | 7/1915 | Smith |
| 1,599,959 A | | 9/1926 | Buheiji |
| 1,732,566 A | | 10/1929 | McKendrick |
| 2,151,418 A | | 3/1939 | Bolté |
| 2,185,927 A | | 6/1940 | Shelanski |
| 2,478,715 A | | 8/1949 | Schmitt |
| 2,623,519 A | | 12/1952 | Cohen |
| 3,057,349 A | * | 10/1962 | Ismach ............... A61D 7/00 604/71 |
| 3,578,215 A | | 5/1971 | Bushnell |
| 3,669,113 A | | 6/1972 | Altounyan et al. |
| 3,940,061 A | | 2/1976 | Gimple et al. |
| 4,184,258 A | | 6/1980 | Barrington et al. |
| 4,427,450 A | | 1/1984 | Kostansek |
| 4,457,329 A | | 7/1984 | Werley et al. |
| 4,806,167 A | | 2/1989 | Raythatha |
| 5,215,221 A | | 6/1993 | Dirksing |
| 5,231,983 A | | 8/1993 | Matson et al. |
| 5,273,531 A | | 12/1993 | Knoepfler |
| 5,310,407 A | | 5/1994 | Casale |
| 5,312,331 A | | 5/1994 | Kneopfler |
| 5,312,333 A | | 5/1994 | Churinetz et al. |
| 5,366,122 A | | 11/1994 | Guentert et al. |
| 5,415,631 A | | 5/1995 | Churinetz et al. |
| 5,445,612 A | | 8/1995 | Terakura et al. |
| 5,470,311 A | | 11/1995 | Setterstrom et al. |
| 5,545,150 A | | 8/1996 | Danks et al. |
| 5,884,621 A | | 3/1999 | Matsugi et al. |
| 5,951,531 A | | 9/1999 | Ferdman et al. |
| 5,989,215 A | | 11/1999 | Delmotte et al. |
| 6,003,512 A | | 12/1999 | Gerde |
| 6,484,750 B1 | | 11/2002 | Foos et al. |
| 6,554,022 B2 | | 4/2003 | Wakeman |
| 6,589,087 B2 | | 7/2003 | Mackal et al. |
| 6,684,917 B2 | | 2/2004 | Zhu et al. |
| 6,708,712 B2 | | 3/2004 | Wakeman |
| 6,716,190 B1 | | 4/2004 | Glines et al. |
| 6,799,571 B1 | | 10/2004 | Hughes et al. |
| 7,178,547 B2 | | 2/2007 | Mackal |
| 7,311,270 B2 | | 12/2007 | Kapila |
| 7,334,598 B1 | | 2/2008 | Hollars |
| 7,361,300 B2 | | 4/2008 | Kelly et al. |
| 7,427,607 B2 | | 9/2008 | Suzuki |
| 7,455,248 B2 | | 11/2008 | Kablik et al. |
| 7,461,649 B2 | | 12/2008 | Gamard et al. |
| 7,465,287 B2 | | 12/2008 | James |
| 7,544,177 B2 | | 6/2009 | Gertner |
| 7,563,299 B2 | | 7/2009 | Baptista da Costa et al. |
| 7,673,647 B2 | | 3/2010 | Mackal |
| 7,841,338 B2 | | 11/2010 | Dunne et al. |
| 7,892,205 B2 | | 2/2011 | Palasis et al. |
| 7,921,874 B2 | | 4/2011 | Tekulve et al. |
| 8,037,880 B2 | | 10/2011 | Zhu et al. |
| 8,057,459 B2 | | 11/2011 | Rioux et al. |
| 8,097,071 B2 | | 1/2012 | Burgess et al. |
| 8,118,777 B2 | | 2/2012 | Ducharme et al. |
| 8,269,058 B2 | | 9/2012 | McCarthy et al. |
| 8,313,474 B2 | | 11/2012 | Campbell et al. |
| 8,360,276 B2 | | 1/2013 | Rogier et al. |
| 8,361,054 B2 | | 1/2013 | Ducharme et al. |
| 8,496,189 B2 | | 7/2013 | Lomond et al. |
| 8,673,065 B2 | | 3/2014 | Burgess et al. |
| 8,721,582 B2 | | 5/2014 | Ji |
| 8,728,032 B2 | | 5/2014 | Ducharme et al. |
| 8,741,335 B2 | | 6/2014 | McCarthy |
| 8,827,980 B2 | | 9/2014 | Ji |
| 8,910,627 B2 | | 12/2014 | Iwatschenko et al. |
| 8,951,565 B2 | | 2/2015 | McCarthy |
| 9,028,437 B2 | | 5/2015 | Ott et al. |
| 9,089,658 B2 | | 7/2015 | Dunne et al. |
| 9,101,744 B2 | | 8/2015 | Ducharme |
| 9,107,668 B2 | | 8/2015 | Melsheimer et al. |
| 9,132,206 B2 | | 9/2015 | McCarthy |
| 9,204,957 B2 | | 12/2015 | Gregory et al. |
| 9,205,170 B2 | | 12/2015 | Lucchesi et al. |
| 9,205,207 B2 | | 12/2015 | Ji |
| 9,205,240 B2 | | 12/2015 | Greenhalgh et al. |
| 9,308,584 B2 | | 4/2016 | Burgess et al. |
| 9,310,812 B2 | | 4/2016 | Costle et al. |
| 9,375,533 B2 | | 6/2016 | Ducharme et al. |
| 9,492,646 B2 | | 11/2016 | Hoogenakker et al. |
| 9,517,976 B2 | | 12/2016 | Mackal |
| 9,545,490 B2 | | 1/2017 | Iwatschenko et al. |
| 9,555,185 B2 | | 1/2017 | Foster et al. |
| 9,629,966 B2 | | 4/2017 | Ji |
| 9,636,470 B2 | | 5/2017 | Pohlmann et al. |
| 9,707,359 B2 | | 7/2017 | Kubo |
| 9,713,682 B2 | | 7/2017 | Eistetter et al. |
| 9,717,897 B2 | | 8/2017 | Rogier |
| 9,821,084 B2 | | 11/2017 | Diegelmann et al. |
| 9,839,772 B2 | | 12/2017 | Ducharme |
| 9,839,774 B2 | | 12/2017 | Bonaldo |
| 9,846,439 B2 | | 12/2017 | Carman et al. |
| 9,867,931 B2 | | 1/2018 | Gittard |
| 9,976,660 B2 | | 5/2018 | Stanton et al. |
| 10,004,690 B2 | | 6/2018 | Lee et al. |
| 10,010,705 B2 | | 7/2018 | Greenhalgh et al. |
| 10,017,231 B2 | | 7/2018 | Fawcett, Jr. |
| 10,036,617 B2 | | 7/2018 | Mackal |
| 10,065,004 B2 | | 9/2018 | Eder et al. |
| 10,173,019 B2 | | 1/2019 | Kaufmann et al. |
| 10,384,049 B2 | | 8/2019 | Stanton et al. |
| 10,441,761 B2 | * | 10/2019 | Christakis ............. A61M 13/00 |
| 10,463,811 B2 | | 11/2019 | Lee et al. |
| 10,507,293 B2 | | 12/2019 | Goodman et al. |
| 10,646,706 B2 | | 5/2020 | Rogier |
| 10,730,595 B2 | | 8/2020 | Fawcett |
| 10,751,523 B2 | | 8/2020 | Rogier |
| 10,806,853 B2 | | 10/2020 | Gittard |
| 10,850,814 B2 | | 12/2020 | Fawcett |
| 10,994,818 B2 | | 5/2021 | Hernandez |
| 11,433,223 B2 | * | 9/2022 | Christakis ........... A61M 31/002 |
| 2004/0107963 A1 | | 6/2004 | Finlay et al. |
| 2004/0249359 A1 | | 12/2004 | Palasis et al. |
| 2005/0121025 A1 | | 6/2005 | Gamard et al. |
| 2005/0147656 A1 | | 7/2005 | McCarthy et al. |
| 2005/0205087 A1 | | 9/2005 | Kablik et al. |
| 2005/0220721 A1 | | 10/2005 | Kablik et al. |
| 2006/0004314 A1 | | 1/2006 | McCarthy et al. |
| 2006/0213514 A1 | | 9/2006 | Price et al. |
| 2007/0056586 A1 | | 3/2007 | Price et al. |

(56) References Cited

U.S. PATENT DOCUMENTS

| | | |
|---|---|---|
| 2007/0066920 A1 | 3/2007 | Hopman et al. |
| 2007/0066924 A1 | 3/2007 | Hopman et al. |
| 2007/0082023 A1 | 4/2007 | Hopman et al. |
| 2007/0125375 A1 | 6/2007 | Finlay et al. |
| 2007/0151560 A1 | 7/2007 | Price et al. |
| 2007/0083137 A1 | 8/2007 | Hopman et al. |
| 2007/0199824 A1 | 8/2007 | Hoerr et al. |
| 2008/0021374 A1 | 1/2008 | Kawata |
| 2008/0287907 A1 | 11/2008 | Gregory et al. |
| 2009/0101144 A1 | 4/2009 | Gamard et al. |
| 2009/0155342 A1 | 6/2009 | Diegemann et al. |
| 2009/0281486 A1 | 11/2009 | Ducharme |
| 2010/0121261 A1 | 5/2010 | Kablik et al. |
| 2010/0305505 A1 | 12/2010 | Ducharme et al. |
| 2011/0073200 A1 | 3/2011 | Overvaag et al. |
| 2011/0178495 A1 | 7/2011 | Ji |
| 2011/0274726 A1 | 11/2011 | Guo et al. |
| 2011/0282382 A1 | 11/2011 | McAllister et al. |
| 2011/0308516 A1 | 12/2011 | Price et al. |
| 2013/0218072 A1 | 8/2013 | Kubo |
| 2014/0018621 A1* | 1/2014 | Stout .................. A61M 39/06 600/106 |
| 2014/0271491 A1 | 9/2014 | Gittard et al. |
| 2015/0094649 A1 | 4/2015 | Gittard |
| 2015/0125513 A1 | 5/2015 | McCarthy |
| 2016/0375202 A1 | 12/2016 | Goodman et al. |
| 2017/0106181 A1 | 4/2017 | Bonaldo et al. |
| 2017/0232141 A1 | 8/2017 | Surti et al. |
| 2017/0252479 A1 | 9/2017 | Ji et al. |
| 2017/0296760 A1 | 10/2017 | Lee et al. |
| 2018/0099088 A1 | 4/2018 | Gittard |
| 2018/0193574 A1 | 7/2018 | Smith et al. |
| 2018/0214160 A1 | 8/2018 | Hoskins et al. |
| 2018/0339144 A1 | 11/2018 | Greenhalgh et al. |
| 2019/0134366 A1 | 5/2019 | Erez et al. |
| 2019/0217315 A1 | 7/2019 | Maguire et al. |
| 2019/0232030 A1 | 8/2019 | Pic et al. |
| 2021/0024187 A1 | 1/2021 | Fawcett et al. |
| 2021/0069485 A1 | 3/2021 | Rogier |

FOREIGN PATENT DOCUMENTS

| | | |
|---|---|---|
| EP | 0 121 342 A2 | 10/1984 |
| EP | 3052168 B1 | 11/2019 |
| JP | H07118305 A | 5/1995 |
| WO | 00/12018 A1 | 3/2000 |
| WO | 03013552 A1 | 2/2003 |
| WO | 2004066806 A2 | 8/2004 |
| WO | 2005062896 A2 | 7/2005 |
| WO | 2006071649 A2 | 7/2006 |
| WO | 2006088912 A2 | 8/2006 |
| WO | 2008033462 A2 | 3/2008 |
| WO | 2008/090364 A2 | 7/2008 |
| WO | 2009061409 A1 | 5/2009 |
| WO | 2015050814 A1 | 4/2015 |
| WO | 2016/041443 A1 | 3/2016 |
| WO | 2018157772 A1 | 9/2018 |

OTHER PUBLICATIONS

Giday, Samuel, et al. "Safety analysis of a hemostatic powder in a porcine model of acute severe gastric bleeding." Digestive diseases and sciences 58.12 (2013): 3422-3428.

Giday, Samuel A., et al. "A long-term randomized controlled trial of a novel nanopowder hemostatic agent for control of severe upper gastrointestinal bleeding in a porcine model." Gastrointestinal Endoscopy 69.5 (2009): AB133.

Giday, S. A., et al. "Long-term randomized controlled trial of a novel nanopowder hemostatic agent (TC-325) for control of severe arterial upper gastrointestinal bleeding in a porcine model." Endoscopy 43.04 (2011): 296-299.

Regalia, Kristen, et al. "Hemospray in Gastrointestinal Bleeding." Practical Gastroenterology. Endoscopy: Opening New Eyes, ser. 8, May 2014, pp. 13-24. 8.

Cook Medical. Hemospray Endoscopic Hemostat, Cook, 2014. (7 pages, in English).

"Hemospray Clinical Experience Shows Efficacy of a New Hemostasis Modality—v1", Cook Medical, 2012.

"Hemospray Clinical Experience Shows Efficacy of a New Hemostasis Modality—v2", Cook Medical, 2013.

"Hemospray Clinical Experience Shows Efficacy of a New Hemostasis Modality—v3", Cook Medical, 2014.

Aslanian, Harry R., and Loren Laine. "Hemostatic powder spray for GI bleeding." Gastrointestinal endoscopy 77.3 (2013): 508-510.

Giday, S. A., et al. "Long-term randomized controlled trial of a novel nanopowder hemostatic agent (TC-325) for control of severe arterial upper gastrointestinal bleeding in a porcine model." Endoscopy 43.04 (2011): 296-299. via ResearchGate.

Retsch GmbH Haan. Sieve Analysis: Taking a Close Look at Quality, An Expert Guide to Particle Size Analysis. 2015. (56 pages, in English).

Micromeritics. Density Analysis, 2001. (6 pages, in English).

Micromeritics. "Application Note: Bulk and Skeletal Density Computations for the AutoPore." May 2012. (3 pages, in English).

Arefnia, Ali, et al. "Comparative Study on the Effect of Tire-Derived Aggregate on Specific Gravity of Kaolin." Electronic Journal of Geotechnical Engineering 18 (2013): 335-44.

Kesavan, Jana, et al. "Density Measurements of Materials Used in Aerosol Studies". Edgewood Chemical Biological Center Aberdeen Proving Ground MD, 2000.

\* cited by examiner

DELIVERY DEVICES AND METHODS

CROSS-REFERENCE TO RELATED APPLICATIONS

This application is a continuation of and claims the benefit of priority of U.S. Nonprovisional application Ser. No. 16/650,664, filed Sep. 4, 2019, which is a continuation of and claims the benefit of priority Nonprovisional Patent application Ser. No. 15/637,743, filed on Jun. 29, 2017, which claims the benefit of priority of U.S. Provisional Patent Application No. 62/357,425, filed on Jul. 1, 2016. Each of the above-mentioned applications is herein incorporated by reference in its entirety.

BACKGROUND

Internal tissue may bleed during a non-invasive surgical procedure, making blood loss and visibility important concerns. During some procedures, a hemostatic agent may be applied to the affected bodily tissue to stop the bleed, at least until a more robust method can be used to permanently stop the bleed. These agents are often delivered as powders. Many of these powders are known to agglomerate, or have agglomerative properties, making it more difficult to propel the powder through a lumen of an endoscope for delivery to a treatment site inside the body. For example, the lumen may become blocked by the material. As a result, some effective of hemostatic agents may have disadvantages, for example, by requiring continuous delivery.

SUMMARY

Implementations of the present disclosure relate to exemplary delivery devices, methods, and systems. Numerous implementations of the present disclosure are now described.

One implementation of this disclosure is a device. The device may comprise a flow chamber including an inlet port for receiving a fluid flow in the flow chamber, and an outlet port for exiting a material from the flow chamber. A formation portion of the flow chamber may form a suspension of the material. A collection portion of the flow chamber may direct the suspension toward the outlet port. In some implementations, an amount of the material may collect in the collection portion adjacent the outlet port. The device may comprise an insertion port for permitting insertion of the material into the flow chamber, and/or a pusher operable to move the amount of material through the outlet port.

In some implementations, the outlet port may be in communication with an exit lumen, and an end of the pusher may be movable through a portion of the exit lumen. The formation portion may include a semi-spherical surface defining a volume in which the fluid flow expands, and a semi-frustoconical surface that funnels the suspension towards the collection portion. In some implementations, the pusher may be biased toward the outlet port by a resilient element, and the device may comprise a stopper that holds the resilient element in a compressed position. The stopper may be moveable to release the resilient element. For example, the stopper may be movable between a first position to compress the resilient element, and a second position to release the resilient element. In other implementations, the pusher may, alternatively, be biased away from the outlet port by the resilient element.

The device may comprise a cap operable with the insertion port to permit insertion of a material in the flow chamber when the cap is disengaged with the insertion port, and seal the insertion port when engaged therewith. The cap may not extend into the flow chamber. Alternatively, the cap may have a protrusion that extends into the formation portion of the flow chamber. The protrusion may have an exterior surface contoured to create, with the fluid flow, at least one of a vortex and a turbulent flow in the flow chamber. In other implementations, the device may comprise an impeller mounted in the flow chamber to create and sustain a vortex in the flow chamber when the fluid flow is received therein.

An end of the pusher may be shaped to push a predetermined amount of the material through the outlet port. The flow chamber may be contained in a body of the device, and the pusher may be an elongated rigid body that extends through an opening in the body. For example, the pusher may extend through a reaction chamber in the body. In some implementations, the device may further comprise an engaging structure mounted on the pusher in the reaction chamber, and a resilient element mounted around the pusher between the engaging structure and an internal surface of the reaction chamber. A stopper may be mounted on the pusher outside of the reaction chamber to hold the resilient element in a compressed position when, for example, the stopper is placed against an exterior surface of the body.

Another implementation of this disclosure is a device comprising: a body defining a flow chamber with an inlet port for receiving a fluid flow in the flow chamber; an insertion port on the body for receiving a material in the flow chamber; and an outlet port on the body for exiting the material from the flow chamber. The fluid flow may form a suspension of the material in the flow chamber. An amount of the material may collect in the flow chamber adjacent the outlet port. In some implementations, the fluid flow is operable with an interior surface of the flow chamber to push the amount of material through the outlet port.

In some implementations, the device may further comprise a cap operable to permit insertion of the material in the flow chamber through the insertion port when the cap is disengaged from the body, and seal the insertion port when the cap is engaged with the body. The cap may have a protrusion that extends into the flow chamber to alter the fluid flow in the flow chamber. The protrusion may have an exterior surface contoured to create, with the fluid flow, at least one of a vortex and a turbulent flow in the flow chamber.

The device may comprise an impeller mounted in the flow chamber to create and sustain, with the fluid flow, a vortex in the flow chamber. Implementations of the vortex may be used to push the amount of the material through the outlet port.

In other implementations, the device may further comprise a pusher operable to push the amount of the material through the outlet port. For example, an end of the pusher may be shaped to push a predetermined amount of the material through the outlet port. The pusher may be operable through an opening in the body. In some implementations, the pusher may extend through a reaction chamber in the body, wherein the device further comprises an engaging structure mounted on the pusher in the reaction chamber, and a resilient element mounted around the pusher between the engaging structure and an internal surface of the reaction chamber. The engaging structure may seal the reaction chamber. In some implementations, the body may have a handle portion. The device may further comprise a sheath extending distally from the outlet port. The pusher may be operable to push the amount of material into the sheath, and a distal end of the sheath may include at least one opening configured to distribute the amount of material. The at least one opening may be moveable between an open position and a closed position.

Another implementation of this disclosure is a method of operating a device, which may include a flow chamber with an inlet port and an outlet port. This method may comprise inserting a material into the flow chamber; receiving a fluid flow in the flow chamber through the inlet port; forming a suspension of the material in the flow chamber with the fluid flow; directing a portion of the suspension through the outlet port, wherein an amount of the material collects adjacent the outlet port; and pushing the amount of material through the outlet port.

According to this implementation, the device may include a pusher that may be biased toward the outlet port by a resilient element. In some implementations, the pusher may include a stopper that holds the resilient element in a compressed position, and the pushing step may comprise moving the stopper to fire the pusher through the outlet port. Alternatively, the device may include a pusher that may be biased away from the outlet port by a resilient element, and the pushing step may comprise compressing the biasing element with the pusher. In other implementations, inserting the material in the flow chamber may comprise disengaging a cap from the insertion port to permit insertion of the material in the flow chamber. The method may further comprise engaging the cap with the insertion port to seal the flow chamber.

Another implementation of this disclosure is a device comprising: a body defining a flow chamber with an inlet port for receiving a fluid flow in the flow chamber; an outlet port on the body for exiting the material from the flow chamber; and a sheath including a proximal end attached to the outlet port, and a distal end including at least one sealed opening configured to be unsealed to exit the material. The fluid flow may form a suspension of the material in the flow chamber. An amount of the material may collect in the flow chamber adjacent the outlet port, and the fluid flow may be operable with an interior surface of the flow chamber to push the amount of the material through the outlet port and into the sheath. The at least one sealed opening may include a removable plug or cap. The device may comprise an insertion port for permitting insertion of the material into the flow chamber, and/or a pusher operable to move the amount of material through the outlet port.

It may be understood that both the foregoing summary and the following detailed descriptions are exemplary and explanatory only, neither being restrictive of the inventions claimed below.

BRIEF DESCRIPTION OF THE DRAWINGS

The accompanying drawings are incorporated in and constitute a part of this specification. These drawings illustrate implementations of the present disclosure that, together with the written descriptions, serve to explain the principles of this disclosure.

DETAILED DESCRIPTION

Implementations of the present disclosure are now described with reference to numerous exemplary delivery devices and methods. Some implementations are described with reference to a non-invasive surgical procedure, wherein the delivery device is used with a fluid flow to deliver a material to a treatment site inside a body. For example, an exemplary delivery device may use a fluid flow (e.g., a flow of compressed gas, like air) to deliver a hemostatic powder to the treatment site through a lumen of the endoscope. Any reference to a particular procedure, such as a non-invasive surgical procedure; a particular agent, such as a hemostatic powder; or a particular fluid, such as air, is provided for convenience and not intended to limit the present disclosure unless claimed. Accordingly, the concepts disclosed herein may be utilized for any analogous device, method, or system—medical or otherwise.

The directional terms "proximal" and "distal," and their respective initials "P" and "D," are used to describe relative components and features of the present disclosure. Proximal refers to a position closer to the exterior of the body or a user, whereas distal refers to a position closer to the interior of the body or further away from the user. Appending the initials P or D to an element number signifies its proximal or distal location. Unless claimed, these directional terms and initials are provided for convenience and not intended to limit the present disclosure to a particular direction or orientation. As used herein, the terms "comprises," "comprising," or like variation, are intended to cover a non-exclusive inclusion, such that a device or method that comprises a list of elements does not include only those elements, but may include other elements not expressly listed or inherent thereto. Unless stated otherwise, the term "exemplary" is used in the sense of "example" rather than "ideal."

Figure 1:
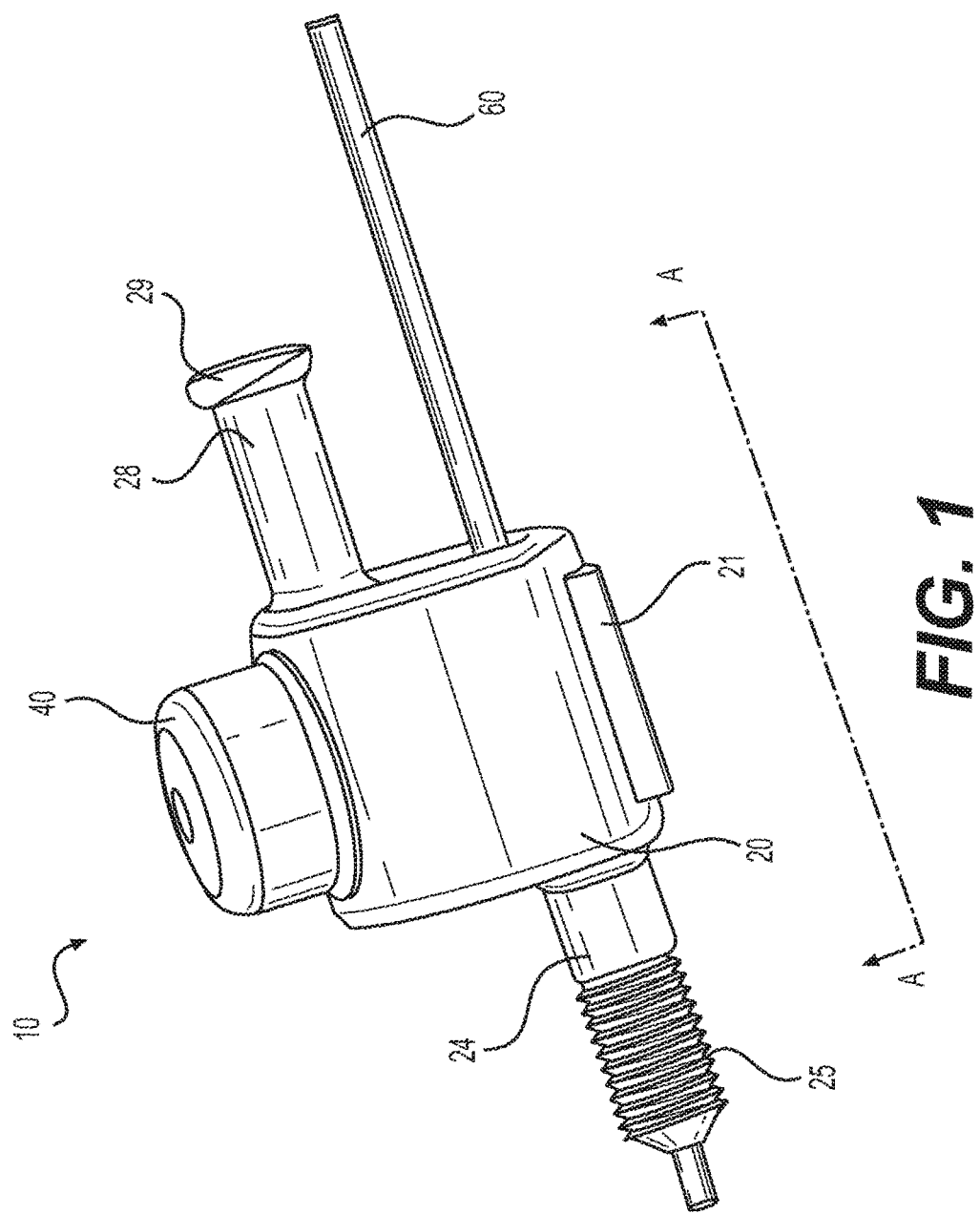
FIG. 1 depicts a perspective view of an exemplary delivery device according to the present disclosure.

Implementations of the present disclosure describe a delivery device 10, such as device 10 of FIG. 1, which depicts a body 20, a cap 40, and a pusher 60. Device 10 may, for example, be coupled to another medical device by a mounting portion 21 of body 10. A fluid flow may be received by inlet port 28 and joined with a material inside a flow chamber 30 (FIG. 2) of body 20 to form a suspension, a portion of which may be moved through an outlet port 24 by the fluid flow and/or pusher 60. Accordingly, the material may be delivered, with device 10, to a treatment site located downstream of outlet port 26. Exemplary materials may include a chitosan, a granular kaolin (e.g., with or without chitosan), a granular smectite, and/or a polysaccharide (e.g., a natural starch and/or sugar), many of which have known agglomerative properties.

Figure 2A:
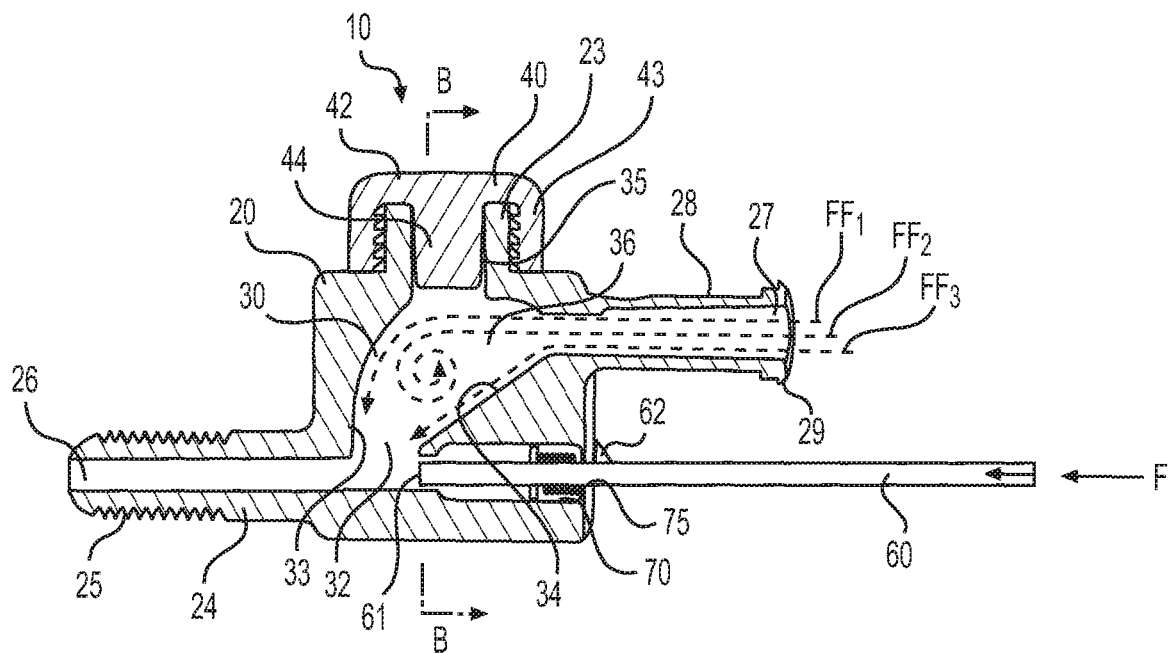
FIG. 2A depicts a section view of the device of FIG. 1 along line A-A.

A section view of device 10 is provided in FIG. 2A to depict an exemplary body 20 as including flow chamber 30 and pusher 60 passing therethrough. As shown in FIG. 2A, flow chamber 30 is in communication with an entry lumen 27 defined by inlet port 28, and an exit lumen 26 defined by outlet port 24. Inlet port 28 and outlet port 24 are each engageable with other elements to create a continuous flow path through device 10. For example, inlet port 28 of FIG. 2A has a ridge 29 configured to receive and retain a tube that is coupled to a source of the fluid flow. In some implementations, ridge 29 is part of a luer connector. Outlet port 24 may be similarly configured. For example, outlet port 24 of FIG. 2A has a set of threads 25 engageable with a fitting of an elongated member extending to the treatment site. In some implementations, threads 25 may be engageable with a part of an endoscope or a catheter. Body 20 further comprises a base portion 21 engageable with another structure, such as a grip handle, or an operating room cart.

Chamber 30 of FIG. 2A includes two portions: a formation portion 36, which causes the suspension; and a collection portion 32, which directs the suspension through exit lumen 26 of outlet port 24. The location of each portions 36, 32 is relative to the locations of outlet and inlet ports 24, 28. For example, formation portion 36 may be adjacent to entry lumen 27, while collection portion 32 is adjacent exit lumen 26. The relative size of portions 36, 32 may vary with the type of material. For example, in FIG. 2A, formation portion 36 may include a majority of the interior surfaces of flow chamber 30, whereas collection portion 32 may be limited to surfaces leading to lumen 26. The respective surfaces of portions 32 and 36 may smoothly transition together; or, alternatively, may include boundary contours that modify implementations of the fluid flow and/or suspension, as described below.

For example, in some implementations, formation portion 36 may include surfaces that cause the fluid flow to assume various flow patterns, such as laminar flow, turbulent flow, vortex flow, or the like. These flow patterns may be used in formation portion 36 to form the suspension. For example, formation portion 36 may cause the fluid flow to form a vortex in chamber 30 that is useful for creating and maintaining the suspension. Collection portion 32 may include surfaces that move (e.g., funnel) a portion of the suspension through exit lumen 26 and out of outlet port 24. Collection portion 32 may also concentrate an amount of the material from the suspension at a location adjacent lumen 26. Accordingly, as in FIG. 2A, collection portion 32 may be further configured to push an amount of the material through lumen 26.

Figure 2B:
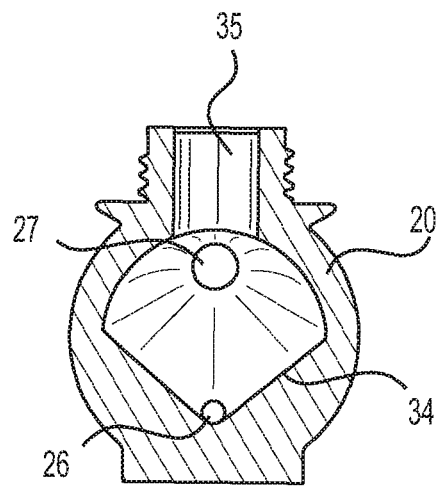
FIG. 2B depicts a section view of the device of FIG. 2A along line B-B.

Formation portion 36 of FIGS. 2A-B, for example, has a funneling surface 34 and a circulating surface 33. Funneling surface 34 is depicted as a semi-frustoconical surface with a minimum width adjacent entry lumen 27 (as measured in FIG. 2B) and a maximum width inside of chamber 30, approximate to the midway point between lumens 26, 27. This configuration allows the fluid flow to expand inside of chamber 30 from a first pressure inside of entry lumen 27 to a second pressure inside of formation portion 36. Circulating surface 33 is depicted as a semi-spherical surface positioned opposite and distal of funneling surface 34. Accordingly, a portion of the fluid flow may travel along the top of funneling surface 34 as a first flow ($FF_1$ in FIG. 2A) before moving across circulating surface 33 and toward collection portion 32; while another portion of the fluid flow may travel along the bottom of funneling surface 34 as a second flow ($FF_2$) moving across surface 34 toward collection portion 32; and yet another portion of the fluid flow moves (e.g., circulates) in a central portion of chamber 30 as a third flow ($FF_3$) before joining one of the first or second flows ($FF_1$ or $FF_2$). Depending upon the source, fluid flows $FF_1$, $FF_2$, and $FF_3$ may be intermittent, pulsed, or continuous.

Figure 4A:
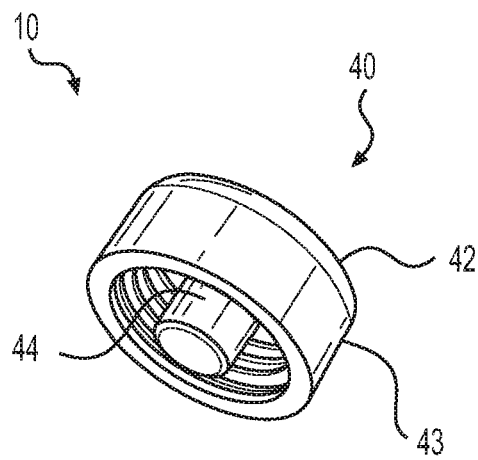
FIG. 4A depicts an exemplary cap for the device of FIG. 1.

The material is inserted in flow chamber 30 by operation of cap 40. In FIGS. 2A-B, body 20 includes a material receiving port 23 that defines a material receiving lumen 35 in communication with flow chamber 30. Cap 40 is removably coupled to material receiving port 23 to permit insertion of the material in chamber 30. For example, the material may be inserted in flow chamber 30 by removing cap 40, and then sealed in chamber 30 by replacing cap 40. As shown in FIGS. 2A and 4A, cap 40 may have a top 42, an edge 43, and a protrusion 44 extending away from top 42. Edge 43 may be removably engageable with material receiving port 23. For example, the interior of edge 43 has a set of threads that are engageable with a corresponding set of threads on the exterior of material receiving port 23 so that cap 40 may be screwed and/or unscrewed from body 20. In FIG. 2A, protrusion 44 is contained entirely in receiving lumen 35 to prevent or at least minimize disruption of any fluid flows (e.g., $FF_1$) inside of flow chamber 30.

The respective funneling and circulating surfaces 34, 33 of flow chamber 30 are, in some implementations, configured to form a suspension of the material in formation portion 36, and direct the suspension toward collection portion 32. For example, a portion of the material inserted through port 23 may be continually mixed by fluid flow $FF_3$ to form and maintain the suspension, while other portions of the material are directed towards collection portion 32 by fluid flows $FF_1$ and $FF_2$. Collection portion 32 of FIG. 2A includes a semi-cylindrical surface aligned with exit lumen 26 to move (e.g., funnel) the suspension into exit lumen 26 using fluid flows $FF_1$ and/or $FF_2$. For some materials, the combined pressure of fluid flows $FF_1$ and $FF_2$ may be sufficient to continuously move the suspension through exit lumen 26, as described below with reference to FIGS. 6A-B. For other materials, however, including agglomerative materials, such as hemostatic agents and like powders, exit lumen 26 may eventually be blocked, or at least constricted, by a mass of the material collected in portion 32 from the suspension as it moves therethrough.

In one solution to this problem, disclosed herein, pusher 60 is operable in collection portion 32 to push an amount of the material into and/or through exit lumen 26, unblocking lumen 26, and allowing said amount of the material to be delivered to a treatment site. As shown in FIG. 2A, pusher 60 may be an elongated, rigid rod that passes through an opening 75 in body 20. Pusher 60 may be operable from a first position, wherein an end 61 of pusher 60 is proximal of exit lumen 26 (e.g., FIG. 2A); to a second position, wherein end 61 is adjacent to and/or inside of exit lumen 26. Accordingly, if an amount of material is disposed in collection portion 32, blocking or at least proximate to exit lumen 26, and in the path of end 61 of pusher 60, then at least some of that amount of material will be pushed into exit lumen 26 by end 61 when pusher 60 is moved to the second position. Exit lumen 26 is then unblocked by returning pusher 60 to the first position, allowing more material to be delivered through lumen 26. In some implementations, end 61 of pusher 60 may be configured to push a predetermined amount (e.g., a dose) of the material through exit lumen 26. For example, an end 61 may have an inclined and/or concave surface contoured to scoop the predetermined amount of the material into lumen 26.

In implementations of this disclosure, a biasing mechanism 70 may be operable with pusher 60. Some types of mechanisms 70 may, for example, fire pusher 60 through the collection portion 32 (e.g., FIG. 3A); automatically retract pusher 60 from collection portion 32 (e.g., FIG. 3B); or otherwise actuate and/or reset pusher 60 in response to a biasing force F (e.g., FIGS. 3A and 3B).

Figure 3A:
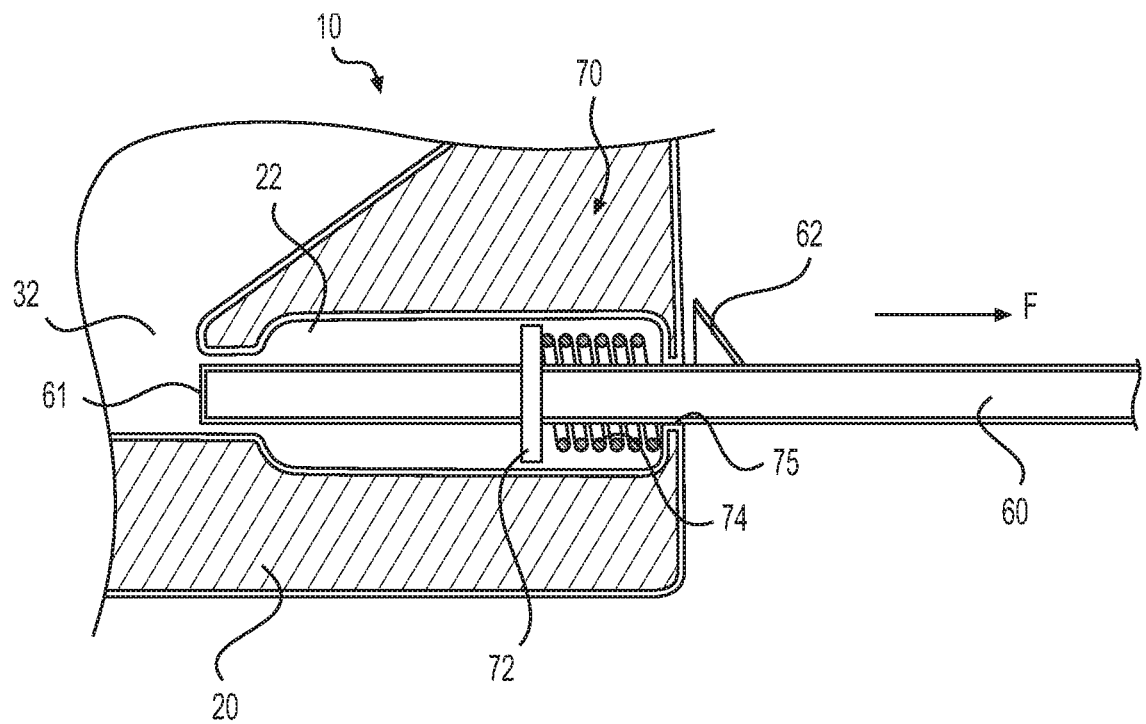
FIG. 3A depicts an exemplary biasing mechanism for the device of FIG. 1.

An exemplary biasing mechanism 70 is depicted in FIG. 3A. As shown, a portion of pusher 60 is housed in a reaction chamber 22 formed in body 20. In FIG. 3A, a stopper 62 is mounted on pusher 60 and positioned outside of chamber 22, adjacent body 20; while an engaging structure (e.g., a reaction disk) 72 is mounted on pusher 60 and positioned inside of chamber 22. A resilient element (e.g., a spring) 74 is disposed between structure 72 and an internal surface of chamber 22 to bias pusher 60 toward exit lumen 26. Stopper 62 holds resilient element 74 in the compressed position so that, upon movement of stopper 62, pusher 60 may be released or fired toward collection portion 32 by allowing resilient element 74 to expand. For example, hole 75 may have a keyhole shape with a central portion and an offshoot. Stopper 62 may be placed in the central portion and propped against body 20 to prevent resilient element 74 from expanding, as shown in FIG. 3A. Conversely, to release or fire, pusher 60 may be rotated until stopper 62 is placed in the offshoot, allowing resilient element 74 to expand against structure 72, pulling stopper 62 into chamber 22, and releasing or firing pusher 60 through the collection portion 32. Pusher 60 may be reset by pulling stopper 62 back through the offshoot, and rotating the stopper 62 back against body 20.

Numerous alternative implementations are now described with reference to device 10 of FIGS. 1-3A and 4A, as well as the devices 110, 210, 310, and 410, which are depicted in or described with reference to FIGS. 3B and 4B-8B. Wherever possible, like element numbers are used to describe like element for each alternative device, but in the 100, 200, 300, or 400 series of numbers relative thereto. Any feature described with reference to any one feature or implementation of particular delivery device 10, 110, 210, etc., may be included or combined with any other feature or implementation disclosed herein, each combination being part of the present disclosure.

Figure 3B:
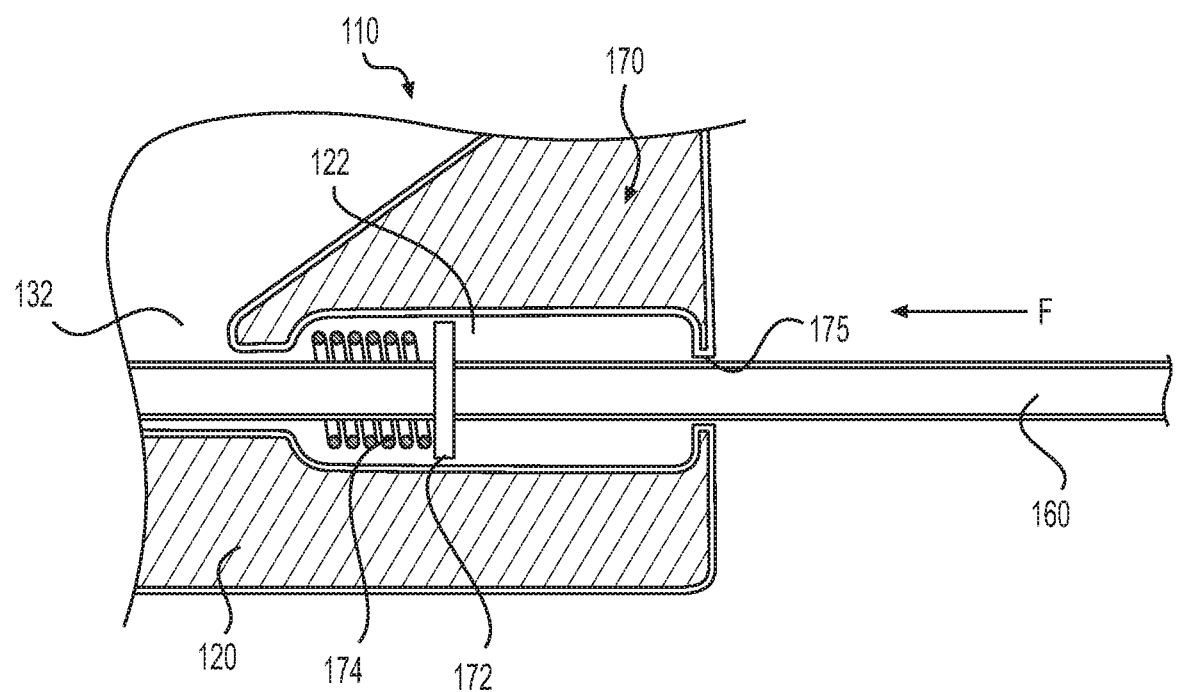
FIG. 3B depicts another exemplary biasing mechanism.
Figure 4B:
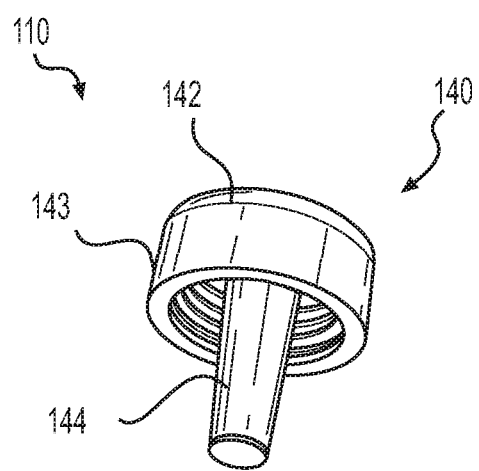
FIG. 4B depicts another exemplary cap for the device of FIG. 1.

Some alternative implementations are illustrated in FIGS. 3B and 4B with reference to a device 110, which may be otherwise similar to device 10. One alternative implementation is depicted in FIG. 3B with reference to a biasing mechanism 170 of device 110. Similar to mechanism 70, mechanism 170 includes a reaction chamber 122 formed in a body 120, and an engaging structure 172 mounted on a pusher 160 and positioned inside of chamber 122. Mechanism 170 also comprises a resilient element 174 (e.g., a spring) disposed between engaging structure 172 and an opposing surface of chamber 122; however, unlike mechanism 70, resilient element 174 is expanded when pusher 160 is in the first position, and compressed when pusher 160 is in the second position (e.g., FIG. 3B). Pusher 160 is, thus, biased away from exit lumen 26 and operable like a trigger. For example, device 110 may be operated by grasping body 120 with a hand, and depressing pusher 160 with a digit (e.g., a thumb). Pusher 160 may be pumped repeatedly, if needed, to deliver amounts of material to the treatment site.

Another exemplary implementation of device 110 is depicted in FIG. 4B with reference to a cap 140. Similar to above, cap 140 may have a top 142, an edge 143, and a protrusion 144 extending away from top 142. The top 142 and edge 143 may function similar to top 42 and edge 43 of cap 40. In this implementation, protrusion 144, when coupled to, for example, material receiving port 23 of a body 20 (FIG. 2A), will extend beyond material receiving lumen 35 and into formation portion 36. For example, protrusion 144 may be long enough to intersect a majority of fluid flows $FF_1$, $FF_2$, and $FF_3$, causing turbulent flow inside of formation portion 36. In some implementations, protrusion 144 is configured to work with the other surfaces of formation portion 36 in, for example, using this turbulent flow to suspend the material, and direct a portion of the suspension toward collection portion 32.

Figure 5:
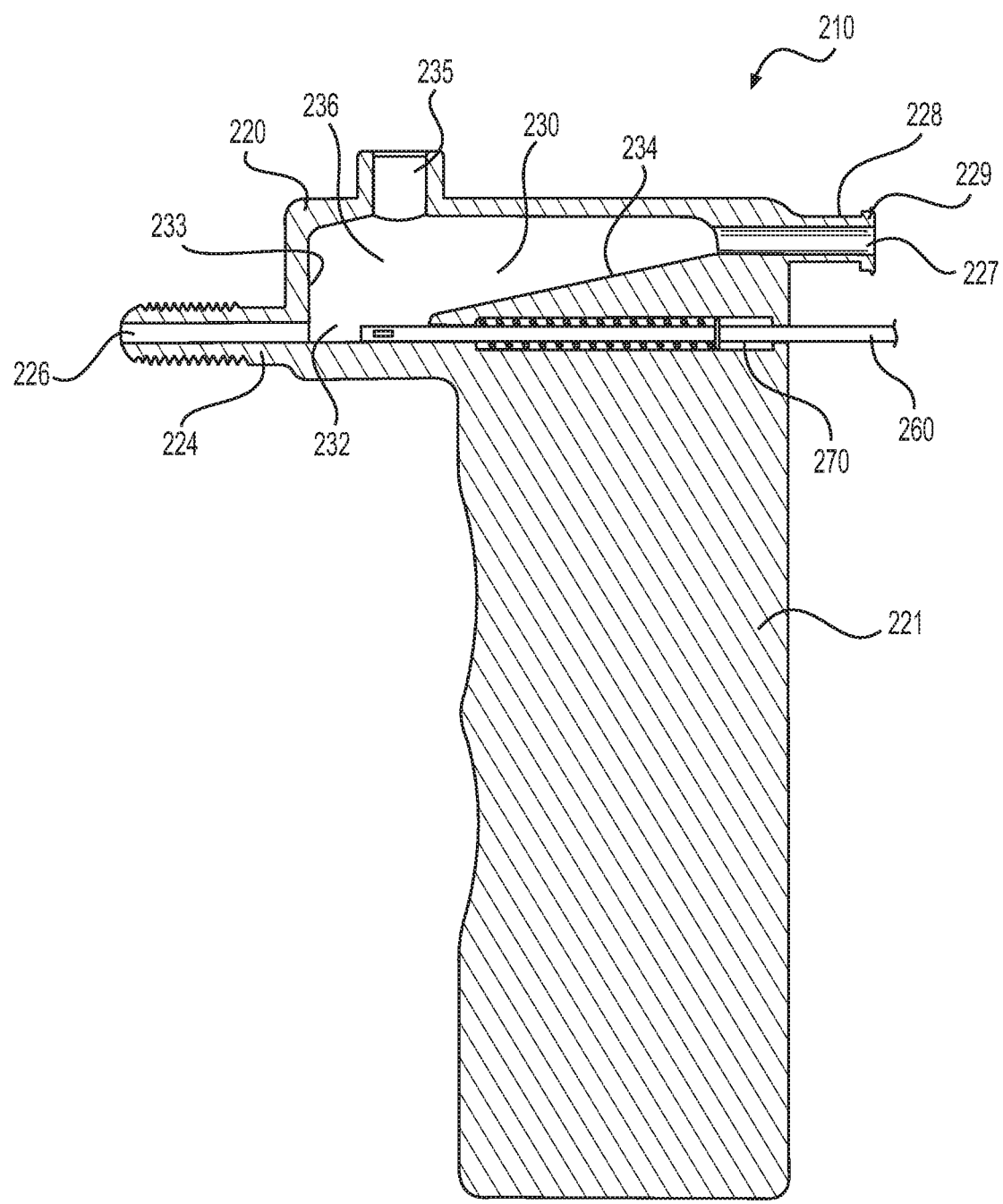
FIG. 5 depicts a section view of another exemplary delivery device according to the present disclosure.

A device 210 is depicted in FIG. 5 as being similar to device 10, except that a flow chamber 230 of device 210 is longer than a corresponding flow chamber 30 of FIG. 2A (relative to the other dimension of chambers 30 and 230); and that a body 220 of device 210 includes a grip portion 221. This first alternative implementation demonstrates that any device 10, 110, 210, etc., may be sized, dimensioned, and/or proportioned to accommodate delivery of a particular material. For example, chamber 230 is longer than chamber 30 (relative to the other dimensions of chamber 30) and, thus, may have an increased volume relative to chamber 30, thereby to increasing the amount of material that may be delivered with device 210 in comparison to device 10. The second alternative demonstrates that body 20, 220, or the like, may vary in shape. Body 220, for example, has grip portion 221 so that device 210 may be grasped by a hand, with grip portion 221 in the palm, and pusher 260 adjacent the thumb. Device 210 includes a biasing mechanism 270 similar to mechanism 170 of FIG. 3B. Accordingly, pusher 260 may be pressed, repeatedly, with the thumb, to deliver amounts of the material.

Figure 6A:
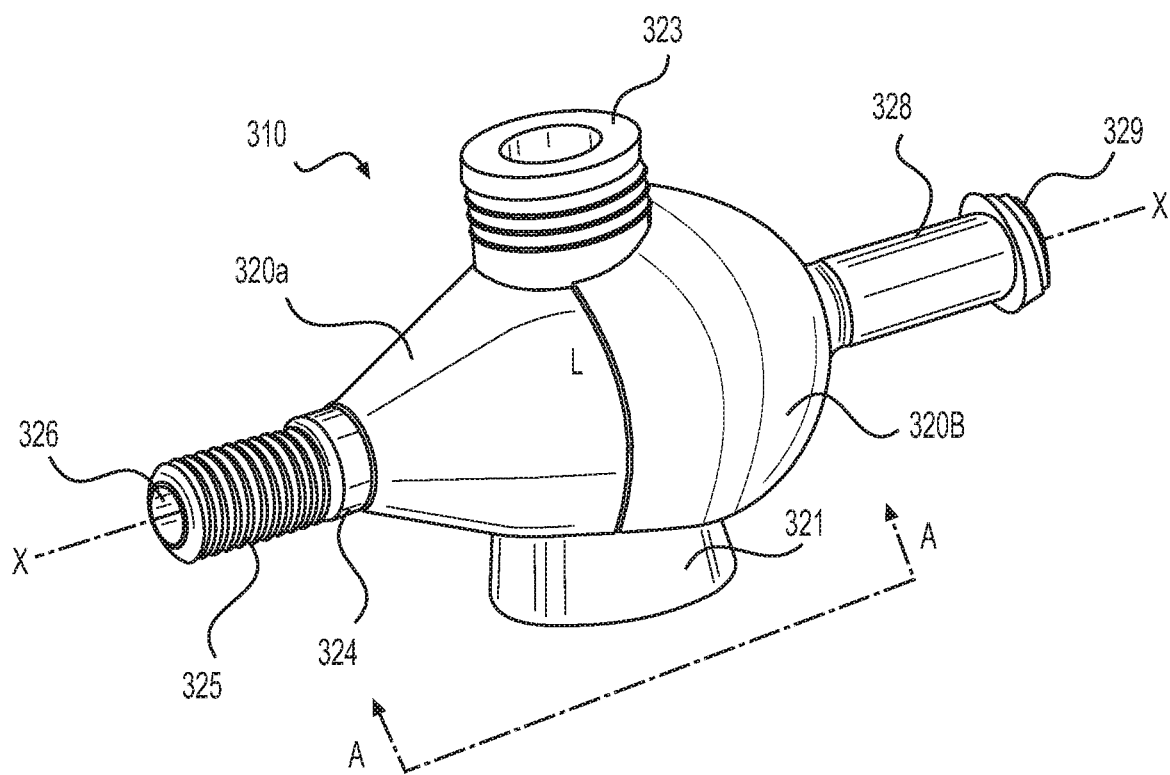
FIG. 6A depicts a perspective view of another exemplary delivery device according to the present disclosure.
Figure 6B:
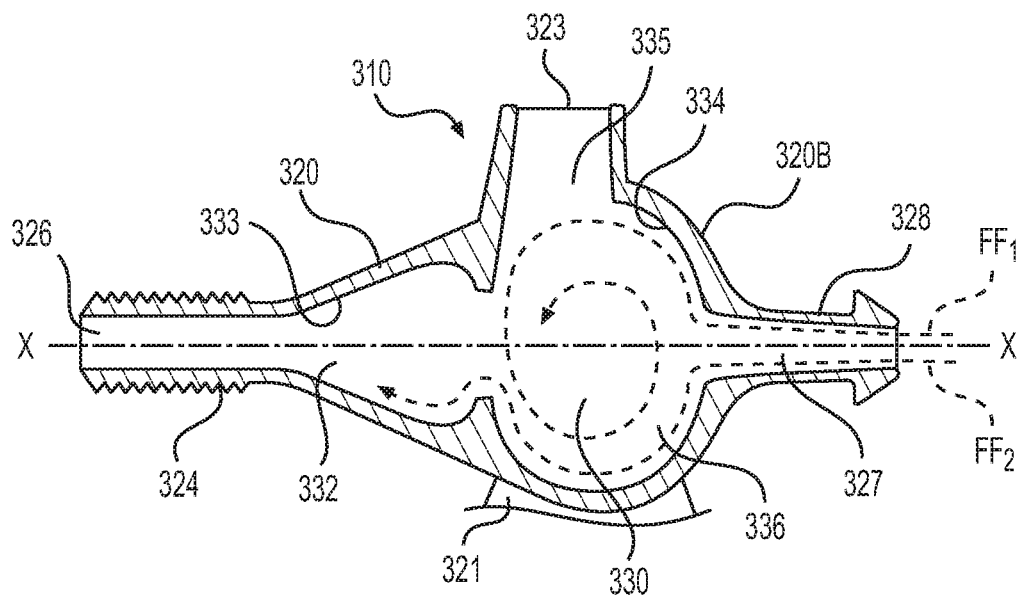
FIG. 6B depicts a section view of the device of FIG. 6A along line A-A.

Other implementations are depicted in FIGS. 6A-B with reference to a device 310, wherein a body 320 and a flow chamber 330 of device 310 are modified to move the suspension through an exit lumen 326 without a pusher. Body 320, for example, has an inlet port 328 and an outlet port 324 aligned along a longitudinal axis X-X of device 310. Flow chamber 330 may be a surface of revolution about axis X-X. For example, as shown in FIG. 6B, flow chamber 330 includes a formation portion 336 having a funneling surface 334 with a semi-spherical shape, and a circulating surface 333 with a semi-frustoconical shape, wherein both shapes are formed as surfaces of revolution around axis X-X. A cap (e.g., similar to cap 40 of FIG. 2A) may be operable with a material receiving port 323 of body 320 to permit insertion of the material in chamber 330. The respect funneling and circulating surfaces 334, 333 of formation portion 336 are configured to suspend the material in the fluid flow, and move the suspension toward collection portion 332 and/or into exit lumen 326. For example, in FIG. 6B, the fluid flow will expand upon entry in formation portion 336, with one portion the fluid flow traveling around the semi-spherical shape of surface 334 as a first flow ("$FF_1$") to create a vortex, and another portion of the fluid flow exiting the vortex as a second flow ("$FF_2$").

Figure 7:
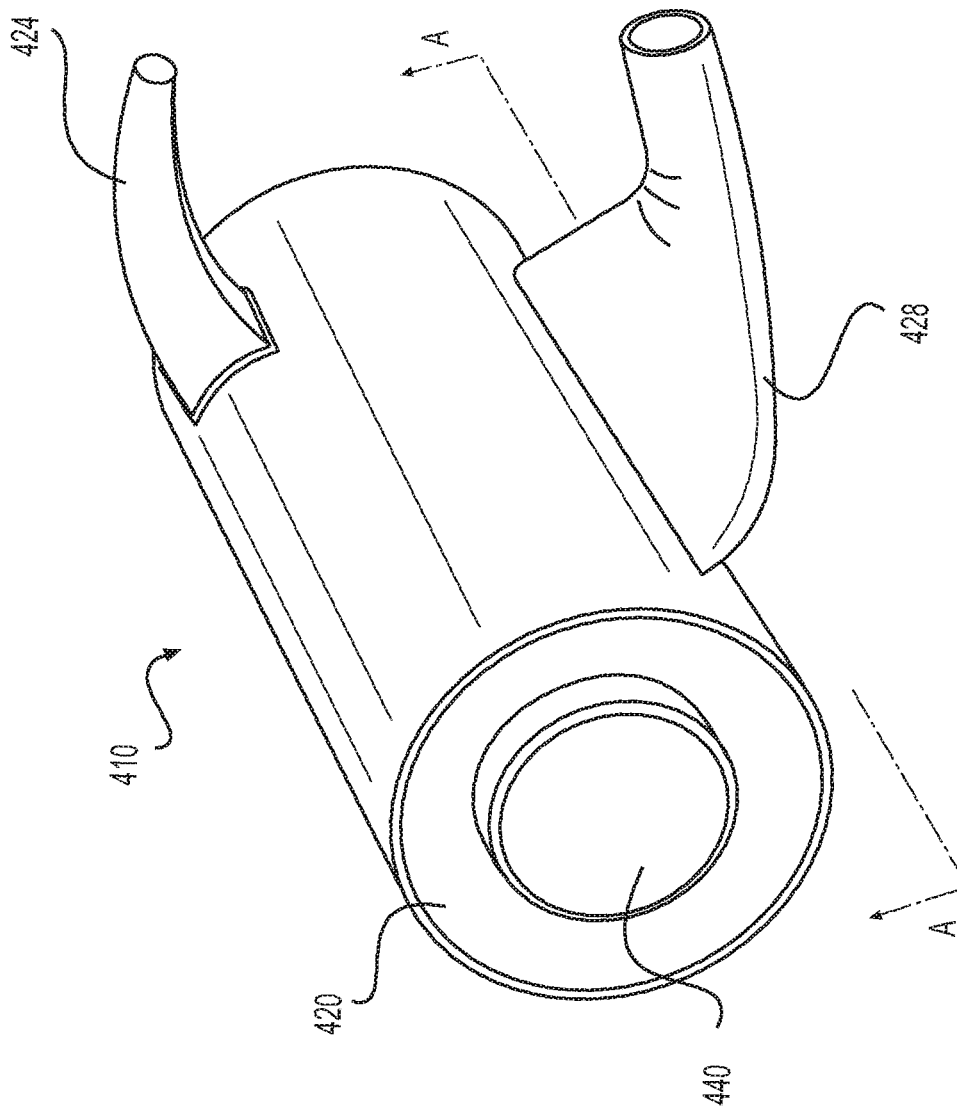
FIG. 7 depicts a perspective view of yet another exemplary delivery device according to the present disclosure.
Figure 8A:
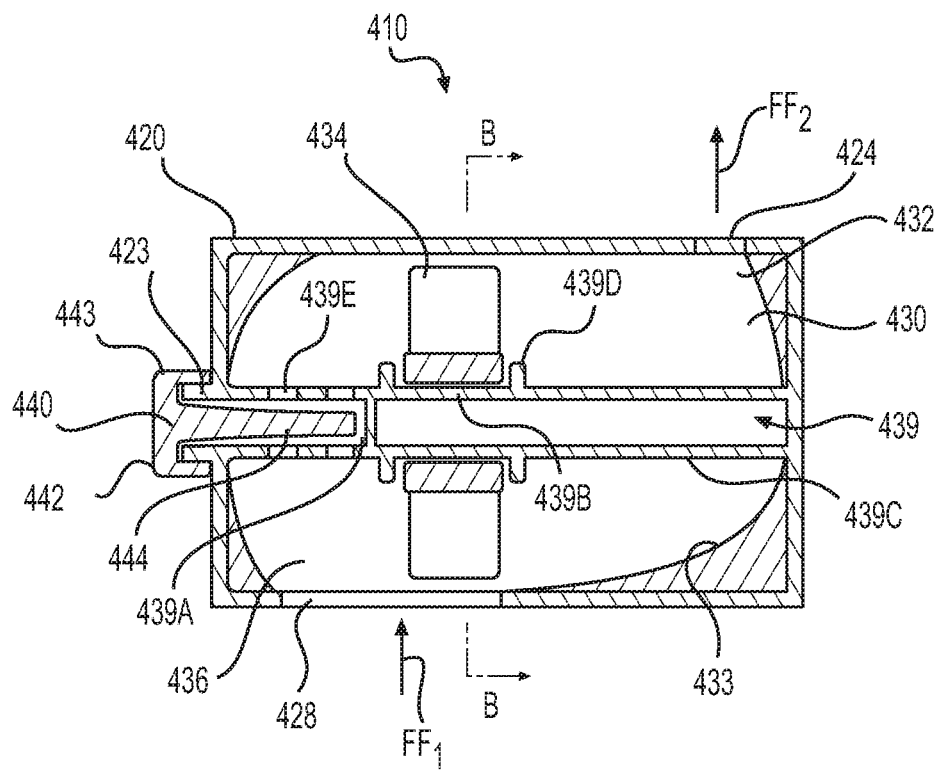
FIG. 8A depicts a section view of the device of FIG. 7 along line A-A.
Figure 8B:
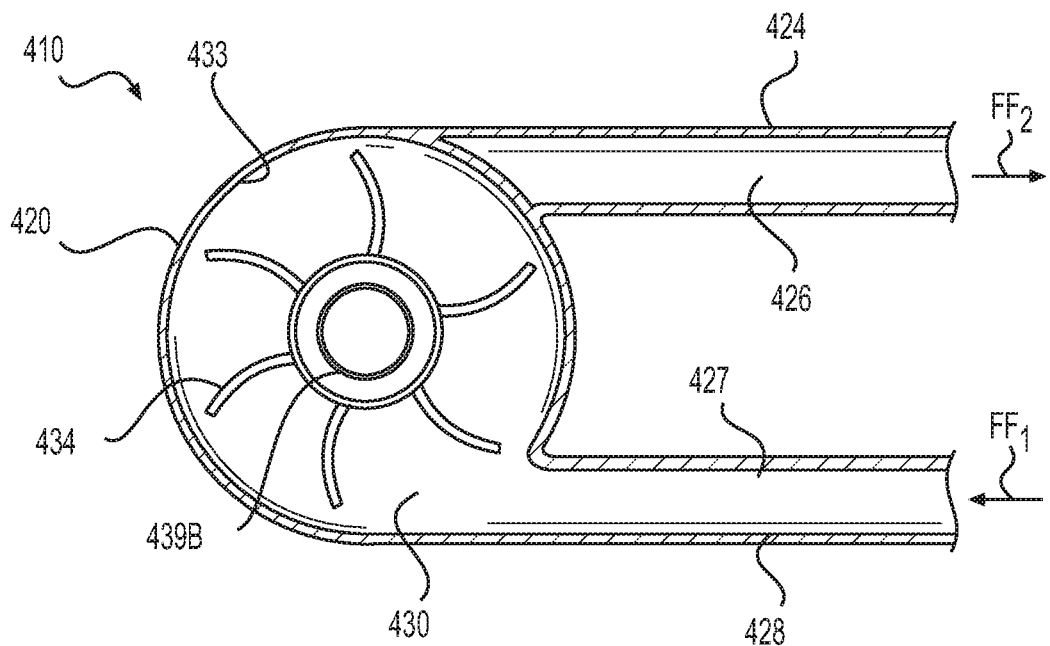
FIG. 8B depicts a section view of the device of FIG. 8A along line B-B.

Other alternative implementations of this disclosure are depicted in FIGS. 7 and 8A-B with reference to a device 410. Similar to above, device 410 of FIG. 7 has a body 420 defining a flow chamber 430; a cap 440 operable to both permit insertion of the material inside of flow chamber 430 and seal the material therein; an inlet port 428 defining an entry lumen 427; and an outlet port 424 defining an exit lumen 426 (both in FIG. 8B). In contrast to above, these elements are arranged about an exemplary impeller 434 location in formation portion 436 of the flow chamber 430 shown in FIGS. 8A-B.

Flow chamber 430 includes a center support 439 with a material holding portion 439A, an impeller support portion 439B, and an end support section 439C. Material holding portion 439A may be configured to receive the material. For example, as in FIG. 8A, body 420 may have a material receiving port 423 extending therethrough into material holding portion 349A. Cap 440 is engaged with material receiving port 423 so that a protrusion 444 of cap 440 extends into material holding portion 439A. The material may, for example, be inserted in holding portion 439A by removing cap 440, sealed in portion 439A and, thus, flow chamber 430 by replacing cap 440, and then distributed through chamber 430 by passing through, for example, one or more perforations 439E formed extending through the exterior wall of holding portion 439A.

Impeller support section 439B provides a surface or axle for impeller 434 to rotate upon. In FIG. 8A, portion 439B includes one or more annular ridges 439D, each ridge 439D being configured to fix the position of impeller 434 in chamber 430. Impeller 434 may rotate on support portion 439B responsive to first fluid flow ("$FF_1$") so that each blade of impeller 434 is utilized to create and sustain a vortex inside of chamber 430. Similar to above, this vortex may be used to form the suspension and move it toward a collection portion 432 and/or through or into exit lumen 426 of chamber 430 as a second fluid flow ("$FF_2$"). The remaining surfaces of flow chamber 430 may also be configured to form the suspension, and deliver of the suspension through exit lumen 426. For example, as shown in FIGS. 8A-B, the interior surfaces of flow chamber 430 and/or the exterior surface of support portion 439C may be contoured and/or oriented to direct the suspension toward collection portion 432 and/or into exit lumen 426.

Figure 9:
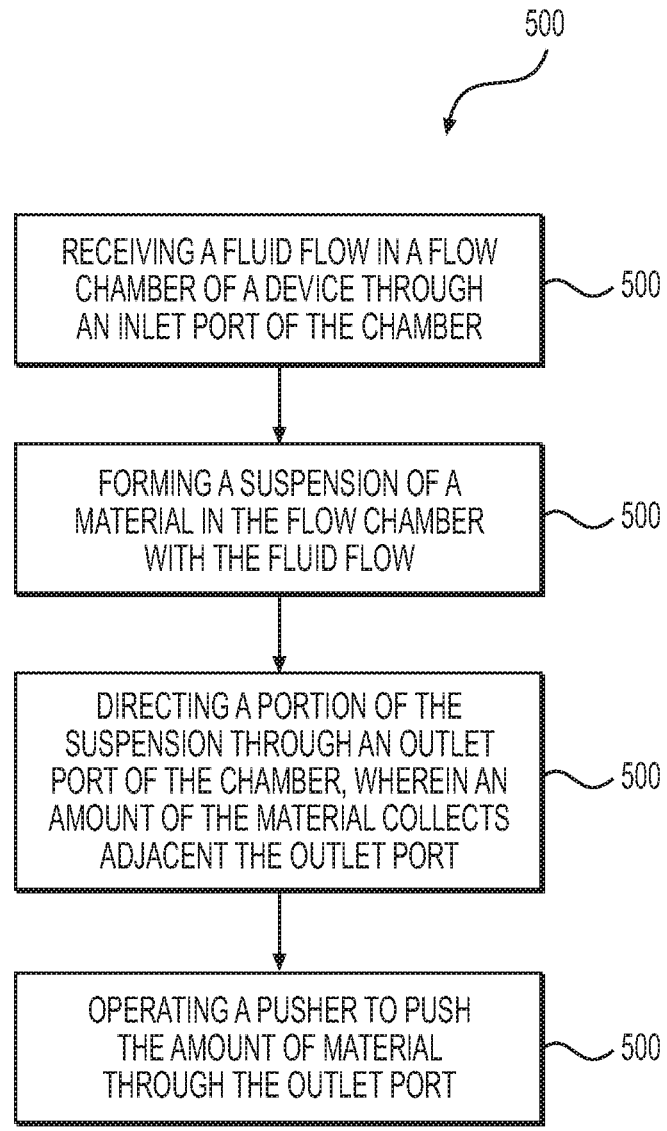
FIG. 9 depicts an exemplary method of operating an exemplary delivery device according to the present disclosure.

Still other implementations are depicted in FIG. 9 with reference to a method 500 for operating any of the devices 10, 110, 210, etc., disclosed herein. Method 500 may, for example, be a method of operating device 10, which, as described above, may include a flow chamber 30 with an inlet port 28, an outlet port 24, and a material receiving port 23. Initial configuration steps may be included in method 500, such as providing device 10 and the material, coupling ports 28 and 24 to other elements to establish a continuous flow path, and the like. For example, these initial steps may include coupling inlet port 28 to a pressurized source of fluid, and connecting outlet port 24 to a port on a medical device, such as an endoscope or catheter. An additional configuration step may include inserting the material into flow chamber 30 through material receiving port 23. Cap 40 may be coupled to port 23, as described above. Accordingly, this additional configuration step may further include operating cap 40 to insert the material.

A step 502 of method 500 may comprise receiving the fluid flow in flow chamber 30 through inlet port 28. For example, the fluid flow may be compressed air that originates from a source, such that step 502 includes the intermediate step of activating the source. A step 504 may comprise forming, with formation portion 36, a suspension of the material in flow chamber 30 with the fluid flow. For example, step 504 may include moving the fluid flow across funneling surface 34 and/or circulating surface 33 to create a fluid flow (e.g., laminar, turbulent, vortex, or the like), and using said fluid flow to form the suspension.

Once the suspension is formed, then a step 506 may comprise directing, with a collection portion 32 of the flow chamber 30, a portion of the suspension through the outlet port 28, wherein an amount of the material may collect adjacent port 28. For example, collection portion 32 is described as having a semi-cylindrical surface aligned with exit lumen 26. If the material is agglomerative, then this surface may collect an amount of material from the suspension as it moves toward collection portion 32 and/or into exit lumen 26. In some implementations, these amounts of material may accumulate in collection portion 32, blocking exit lumen 26. Thus, another step 508 may comprise operating pusher 60 to push the amount of material through exit lumen 26.

Implementations of method 500 may be modified for use with any device 10, 110, 210, etc., disclosed herein. For example, the formation step 504 may be modified to accommodate the elongated protrusion 144 of cap 140 (FIG. 3B), or the varied shapes and surfaces of flow chamber 330 (FIG. 6B). Pusher 60 may be operated differently in step 508, depending upon the biasing mechanism 70 employed. For example, in device 10, pusher 60 may be fired toward collection portion 32 by resilient element 74. Accordingly, step 508 may include moving stopper 26 a first time to release pusher 60, and moving stopper 26 a second time to reset pusher 60. In other implementations, pusher 60, and thus step 508, may omitted entirely, as with device 310 of FIGS. 6A-B. Similar modifications for method 500 are contemplated for device 410 of FIGS. 8A-B. For example, the initial configuration steps may be modified to distribute the material with material holding portion 439A. The forming step 504 and directing step 506 may be similarly modified for use with impeller 434 described above.

Still other implementations may be realized by omitting or combining the features of the various delivery devices disclosed herein. For example, a cap 40 has been described with respect to device 10, yet may be omitted from device 10 if the material is otherwise placed or sealed inside of flow chamber 30, as may occur of the device 10 is intended for single-use. Any device disclosed herein may include pusher 60, which may be operable with biasing mechanism 70, 170, or like mechanisms; or omit pusher 26, as with device 310, wherein flow chamber 330 is configured to move the suspension through exit lumen 326. Although described with reference to device 410, impeller 434 may be used with any disclosed device. For example, any of flow chambers 30, 130, 230, or 330 may be modified to accommodate impeller 434 for the purpose of forming, maintaining, and/or directing the suspension, with or without the aid of a pusher.

Figure 10:
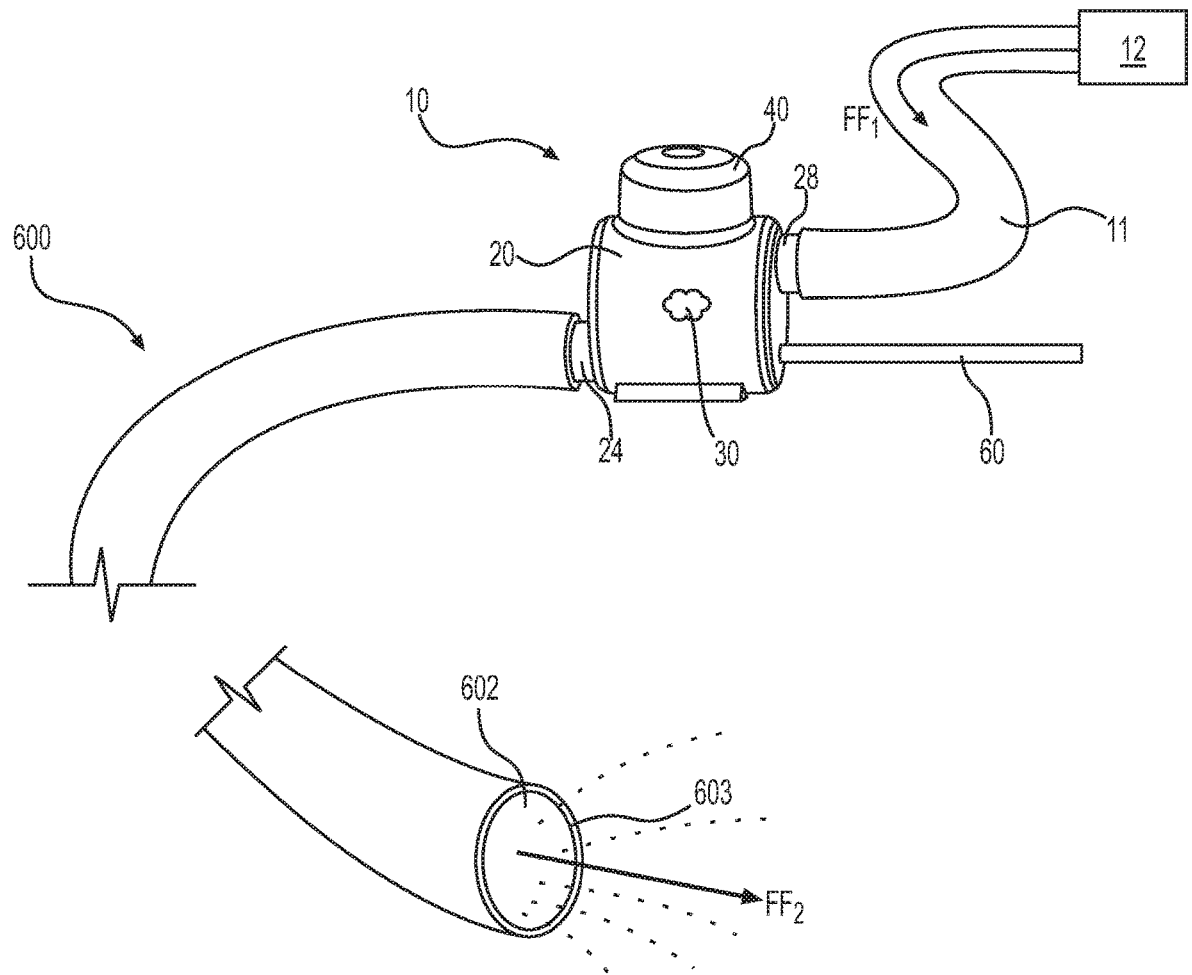
FIG. 10 depicts an exemplary system including a delivery device according to the present disclosure, and a sheath extending distally from said device.

Another implementation of the present disclosure may include device 10 described above; and a sheath 600 including a sheath lumen 602 extending between the proximal end distal ends of sheath 600, and a distal end opening 603 at the distal end of sheath 600. In FIG. 10, a source element 12 is coupled to inlet port 28 of device 10 by a supply line 11; and sheath 600 of FIG. 10 extends distally from outlet port 24 of device 10. Source element 12 may be a fluid pump configured to deliver a first fluid flow $FF_1$ into chamber 30 through supply line 11. Implementations of chamber 30 may be utilized to modify first fluid flow $FF_1$, as described above, into a second fluid flow $FF_2$ delivered to sheath lumen 602 through outlet port 24. The first flow $FF_1$ may include a stream of air and/or other medical gas; and the second fluid flow $FF_2$ may include the material from chamber 30 (e.g., any of the agglomerative materials described herein).

Over time, the material from chamber 30 may block outlet port 24. Device 10 may be operable to unblock outlet port 24. As shown in FIG. 10, for example, device 10 may include a pusher 60 operable to push the material out of port 24 and into sheath lumen 602. The distal end opening 603 of sheath lumen 602 also may be blocked by the material. For example, sheath 600 may be inserted into a body cavity, exposing distal end opening 603 as well as distal portions sheath 600 and lumen 602 to bodily fluids (e.g., blood and/or saline) that may attract the material, eventually forming a blockage within lumen 602 at a location proximate to distal end opening 603. Sheath 600 may be configured to inhibit or prevent formation of the blockage. As shown in FIG. 10, for example, distal portions of sheath lumen 602 (e.g., portions proximate to distal end opening 603) may include a hydrophobic material layer, and proximal portions of lumen 602 (e.g., portions proximal of said distal portions) may include an anti-static material layer. The hydrophobic layer may be configured to repel the fluid, and the anti-static layer may be configured to repel the material, preventing the material from gathering inside of and eventually blocking distal end opening 603.

Figure 11A:
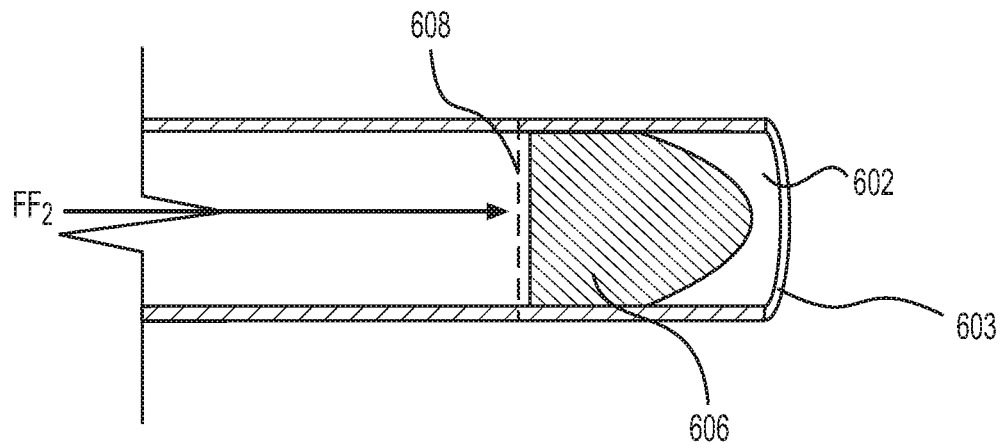
FIG. 11A depicts a section view of the sheath of FIG. 10 including an exemplary distal end of the sheath, and an exemplary plug at said distal end.
Figure 11B:
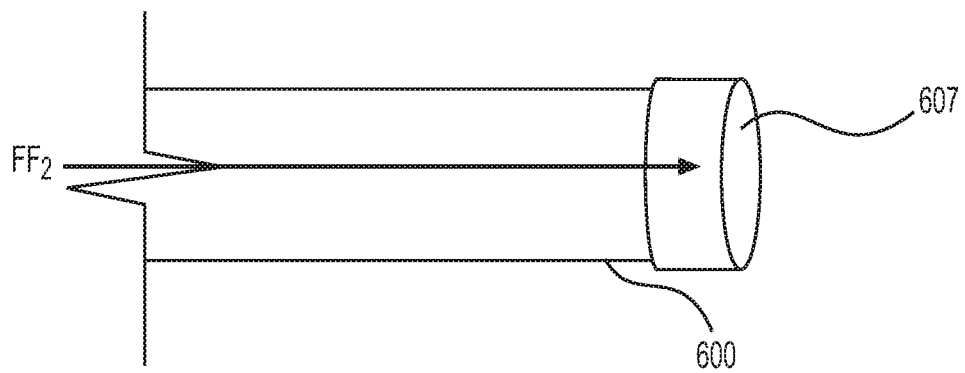
FIG. 11B depicts a side view of the sheath of FIG. 10 including the distal end of the sheath, and an exemplary cap at said distal end.

As shown in FIG. 11A, a plug 606 may be used to seal the distal end opening 603 of sheath lumen 602. Plug 606 may be coupled to interior surfaces of sheath lumen 602. For example, at least a portion of plug 606 may include an expandable material configured to achieve a friction fit with the interior surfaces of lumen 602 when expanded therein. The shape of plug 606 may vary. For example, plug 606 may have a spherical or cylindrical shape, as shown in FIG. 11A. Alternatively or additionally, a cap 607 also may be used to seal the distal end opening 603 of sheath lumen 602. Cap 607 may be coupled to the exterior surfaces of sheath 600. As shown in FIG. 11B. For example, cap 607 may include an annular receiving portion that is snap-fit over or friction-fit with the distal end of sheath 600. Cap 607 also may include a thread engageable with a corresponding thread on sheath 600. Implementations of plug 606 and cap 607 may be combined. For example, an expandable portion of cap 607, such as a cylindrical protrusion extending proximally from a proximal surface of cap 607, may be placed inside sheath lumen 602 and configured to achieve a friction fit with lumen 602, similar to plug 606.

All or portions of plug 606 and cap 607 may be made of a dissolvable material. For example, plug 606 and/or cap 607 may be made of a water soluble material configured to dissolve when exposed to the fluid for a period of time, disrupting the friction fit, and allowing plug 606 and/or cap 607 to automatically separate from the lumen 602. Plug 606 and/or cap 607 may be configured to dissolve when contacting certain bodily tissues, such as when being pushed against the mucosa. Plug 606 or cap 607 also may be ejected from lumen 602 by second fluid flow $FF_2$ once the friction fit has been disrupted. As shown in FIG. 11A, sheath 600 may include at least one fracture plane 608 that can be more easily broken or cut when plug 606 cannot otherwise be removed, or if lumen 602 becomes blocked after plug 606 has been removed. Sheath 600 may include a plurality of fraction planes 608.

Figure 12A:
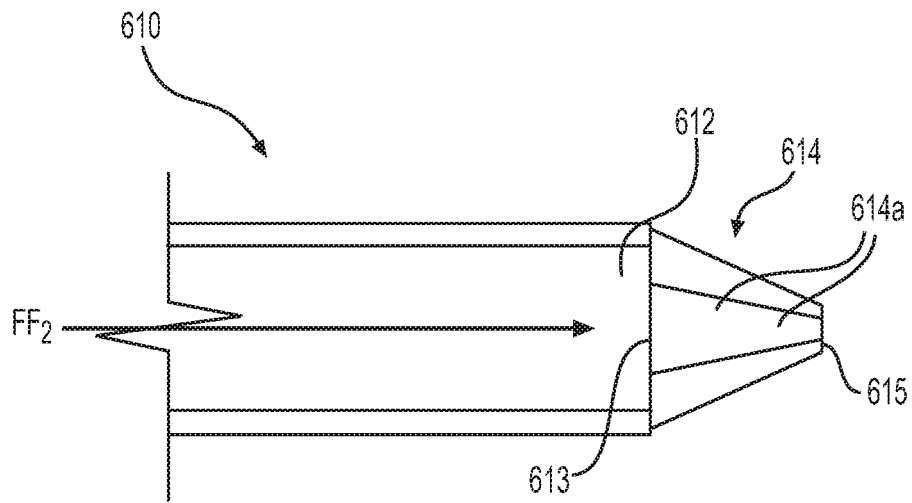
FIG. 12A depicts another exemplary distal end of the sheath of FIG. 10 including an operable end in a closed position.
Figure 12B:
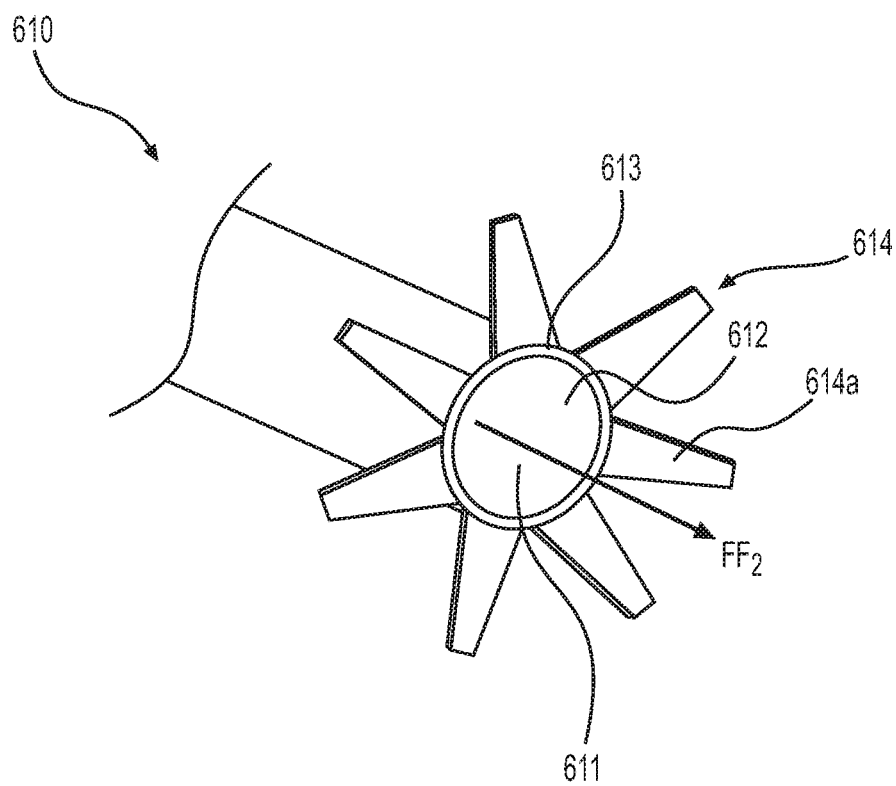
FIG. 12B depicts the operable end of FIG. 12A in an open position.

Another exemplary sheath 610 is depicted in FIGS. 12A-B. As shown, sheath 610 may include a sheath lumen 612, a distal end opening 613, and a valve 614 operable to open or close the distal end opening 613. In FIGS. 12A-B, valve 614 may include a plurality of flaps 614a movable between a closed position, wherein distal end opening 613 is blocked (e.g., FIG. 12A); to an open position, wherein distal end opening 613 is not blocked (e.g., FIG. 12B). Any valve structure may be used. As shown in FIGS. 12A-B, for example, valve 614 may comprise a plurality of triangular shaped flaps 614a with proximal ends attached to sheath 610, and distal ends that converge to define a distal-most end 615 of sheath 600. The proximal ends of each flap 614a may be attached to sheath 610 by a living hinge configured to bias valve 614 toward the open or closed positions. Valve 614 may comprise any number of outwardly or inwardly folding flaps 614a; or any type of single, bi-valve, or tri-valve structure attached to distal portions of sheath 610; any of which may be biased open or closed.

Various means for operating valve 614 are contemplated. Second fluid flow $FF_2$ may be used to operate valve 614. For example, valve 614 may be biased toward the closed position, and then pushed open by second fluid flow $FF_2$. Additional components may be used to operable valve 614. For example, sheath 610 may located in a retaining catheter with a working channel (e.g., similar to working channel 638 of FIGS. 13B-C), valve 614 may be biased toward the open position, and sheath 610 may be moved proximally relative the working channel (or vise versa) to close valve 614. A distal end of the retaining catheter or working channel may be attached to valve 614 for manual operation. For example, sheath 610 may be located in working channel 638 of FIGS. 13B-C, and an exterior portion of each flap 614a depicted in FIG. 12B may be attached to an interior surface of working channel 638, such that sheath 610 may be moved distally relative to channel 638 to open valve 614, or proximally relative to channel 638 to close valve 614. Alternatively, sheath 610 may include guide wire extending along its length (e.g., through another sheath lumen), and the wire may be operable with valve 614 in a similar manner.

Figure 13A:
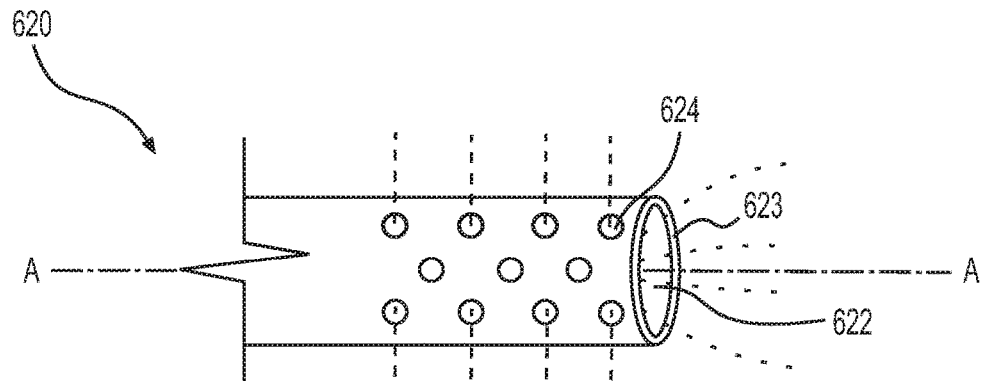
FIG. 13A depicts another exemplary distal end of the sheath of FIG. 10.

Yet another sheath 620 is depicted in FIG. 13A. As shown, sheath 620 may include a sheath lumen 622 with a distal end opening 623, and a plurality of side openings 624 extending through a sidewall of sheath 620 into sheath lumen 622. Distal end opening 623 and/or the plurality of side openings 624 provide numerous exit points for the material from chamber 30, thereby preventing the blockage of distal end opening 623 and/or providing additional delivery means. For example, as shown by the dotted lines in FIG. 13A, a first portion of the material may be delivered through distal end opening 623, and a second portion of the material may be delivered through side openings 624. Openings 623 and 624 may provide different spread patterns for the material. As shown in FIG. 13A, for example, end opening 623 may provide an end-fire configuration; and the side openings 624 may be distributed radially about a longitudinal axis A-A of sheath 620, and arranged transversely with the longitudinal axis A-A to distribute the material in a side-fire configuration with a radial spread pattern.

Figure 13B:
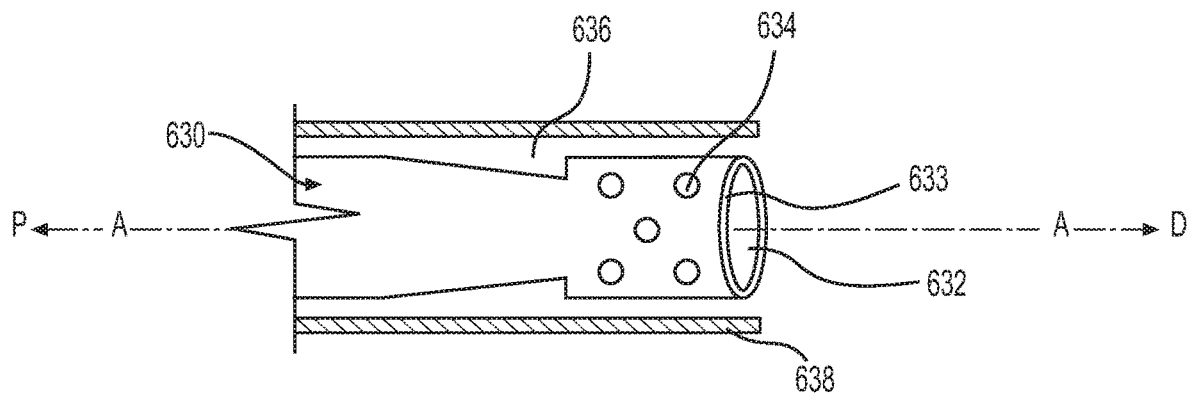
FIG. 13B depicts a section view of a working channel, and another exemplary distal end for the sheath of FIG. 10 inside the working channel.
Figure 13C:
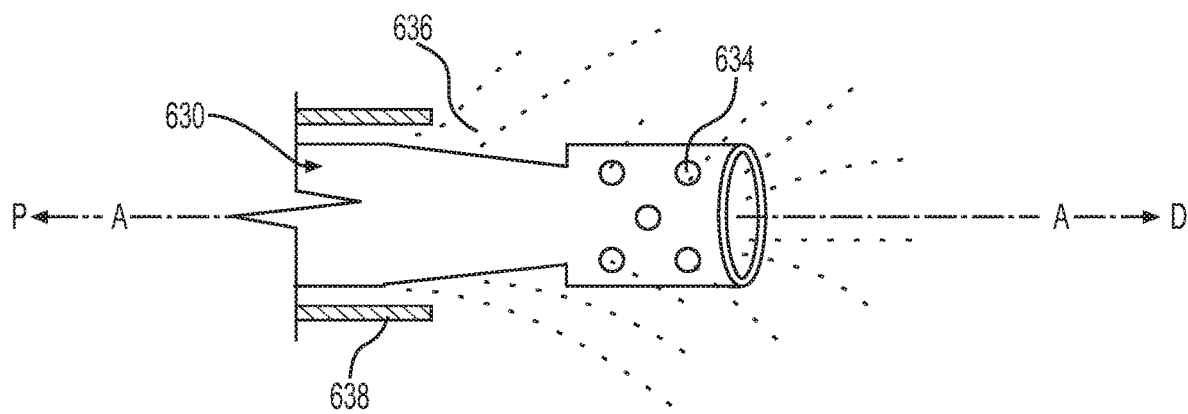
FIG. 13C depicts the distal end of FIG. 13B after being moved outside the working channel.

Additional openings may be provided to modify the spread patterns. For example, another sheath 630 is depicted in FIGS. 13B-C as comprising a sheath lumen 632 with a distal end opening 633, a plurality of side openings 634 extending through a sidewall of sheath 630 into sheath lumen 632, and at least one directional opening 636. Each directional opening 636 may be configured to direct a portion of second fluid flow $FF_2$ out of sheath lumen 632. An opposing pair of directional openings 636 are depicted in FIGS. 13B-C, for example. Each opening 636 may be configured to direct a portion of fluid flow $FF_2$ out of lumen 632 in a distally-directed spread pattern shown, and/or each opening 634 may be configured to direct another portion of fluid flow $FF_2$ out of lumen 632 in a radial spread pattern.

As also shown in FIGS. 13B-C, sheath 630 may be operable within a working channel 638 of a scope, such as ureteroscope; or a retaining catheter, such as a tubing sleeve. For example, as shown in FIG. 13B, sheath 630 may be advanced through working channel 638 until the distal portion of sheath 630 is adjacent a distal portion of working channel 638. In this fully retracted position, openings 634 and 636 are blocked by interior surfaces of working channel 638, preventing entry of fluid into sheath lumen 632. Sheath 630 may be moved relative to working channel 638 in response to an axial and/or rotational force applied to sheath 630 or channel 638. The relative movements may be used to move sheath 630 between various retracted and extended positions. For example, sheath 630 or channel 638 be moved to utilize the different spread patterns described herein.

Figure 14A:
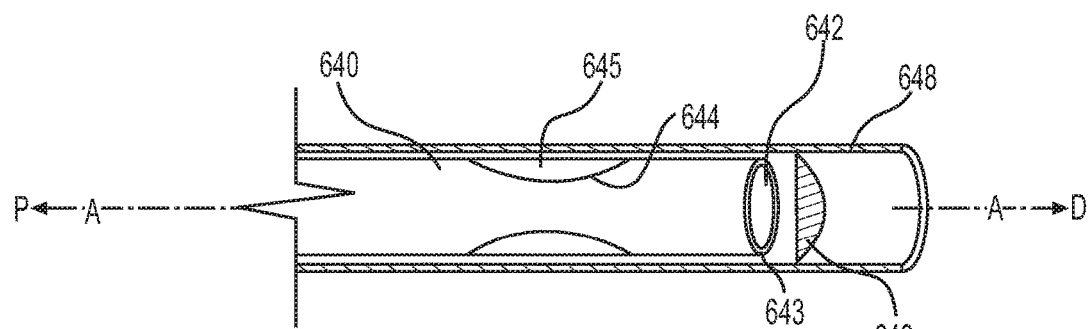
FIG. 14A depicts a section view of a working channel including another exemplary distal end for the sheath of FIG. 10 inside the working channel, and an exemplary plug at a distal end of the working channel.
Figure 14B:
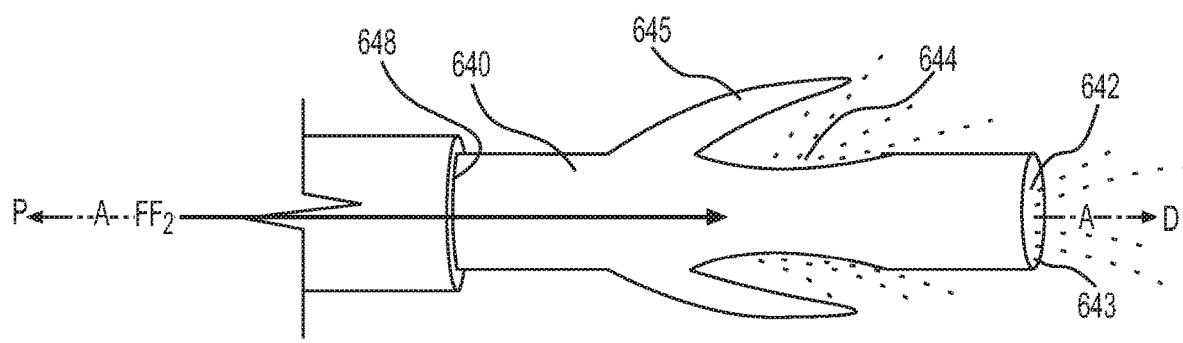
FIG. 14B depicts the distal end of FIG. 14A outside the working channel.

Another sheath 640 is shown in FIGS. 14A-B. Sheath 640 may comprise a sheath lumen 642, a distal end opening 643, and at least one side opening 644 configured to be covered and uncovered by a flap 645. As shown in FIG. 14A, side opening 644 may include two side openings disposed on opposite sides of sheath 640. At least one side flap 645 may cover each side opening 644. Any flap or valve structure may be used. Each side flap 645 may be movable between a closed position, as in FIG. 14A; and an open position, as in FIG. 14B. Flaps 645 may be biased toward the closed position. For example, each flap 645 may be cut-out from the sidewall of sheath 640 to have a semi-circular cross-sectional shape and a living hinge that maintains the flap 645 in the closed position absent fluid flow $FF_2$. As shown in FIGS. 14A-B, sheath 640 may be operable within a working channel 648 of a scope, retaining catheter, or other sheath. The interior diameter of working channel 648 may be sized approximate to the outer diameter of sheath 640 so that the interior surfaces of channel 648 maintain flap 645 in the closed position.

As shown in FIG. 14A, a plug 646 may be been inserted into the distal end of working channel 648 to prevent fluids from entering the distal end opening 643 of sheath 640. For example, distal portions of working channel 648 may be moved into a body cavity, exposing channel 648 to bodily fluids. Plug 646 may be used to prevent those fluids from entering distal end opening 643 until plug 646 has been removed. Plug 646 may be pushed out by sheath 640; blown out by second fluid flow $FF_2$; and/or dissolved, allowing sheath 640 to be moved distally until flaps 645 are moved into and/or maintained in the open position by fluid flow $FF_2$. In some implementations, flaps 645 open automatically with second fluid flow $FF_2$. Flaps 645 also may open automatically whenever distal end opening 643 becomes blocked, ensuring continuous delivery of the material. Flaps 645 may, for example, be moved into the closed position by retracting sheath 640 into working channel 648.

Figure 14C:
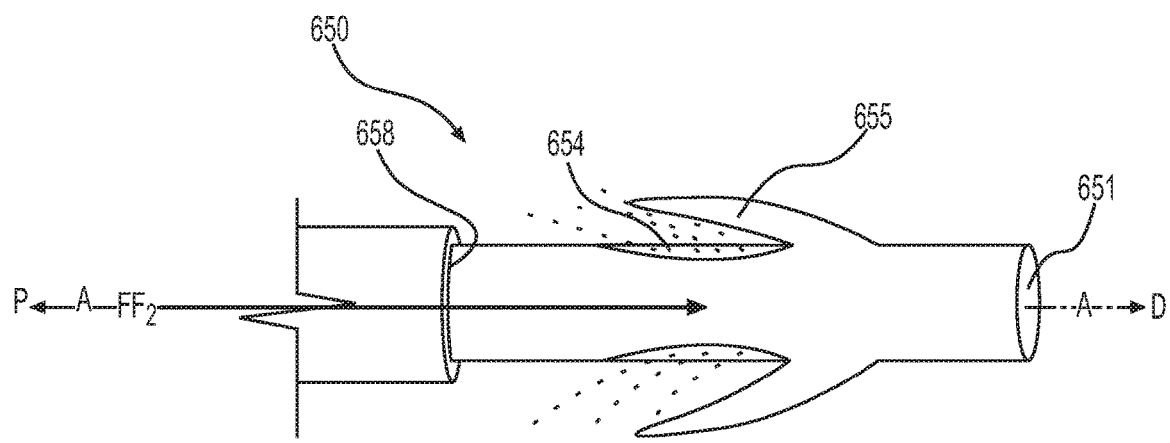
FIG. 14C depicts a side view of a working channel, and another exemplary distal end for the sheath of FIG. 10 outside the channel.

Flaps 645 are distal-facing in FIG. 14B. As shown, the living hinge of each flap 645 is located at the proximal-most end of each flap 645 so that the interior surfaces of flap 645 face distally when flap 645 is opened. Another sheath 650 is depicted in FIG. 14C as having flaps 655 that are proximal-facing. As shown, the living hinge of each flap 655 is located at the distal-most end of each flap 655 so that the interior surfaces of flap 655 face proximally when flap 645 is opened. Flaps 655 of FIG. 14C are otherwise identical to flaps 645 of FIG. 14B.

As shown in FIG. 14C, sheath 650 may include an end plate 651 rather than a distal end opening (e.g., like opening 643 of sheath 640). End plate 651 may be used move sheath 650 distally relative to a working channel 658 by action of second fluid flow $FF_2$ against the proximal surfaces of end plate 651. Flaps 655 may be configured to automatically open once they have been moved distally beyond the distal end of a working channel 658 of a scope, retaining catheter, or other sheath. The distal surfaces of end plate 651 may be used as a stop surface. For example, fluid force $FF_2$ may be delivered at a first flow rate configured to move sheath 650 distally until distal surfaces of end plate 651 make contact with a bodily surface, such as the mucosa; and a second flow rate configured to open flaps 655, allowing for side-fire distribution of the material from a stable point inside the body cavity.

While principles of the present disclosure are disclosed herein with reference to illustrative implementations for particular applications, the disclosure is not limited thereto. Those having ordinary skill in the art and access to the teachings provided herein will recognize additional modifications, applications, aspects, and substitution of equivalents all fall in the scope of the implementations disclosed herein. Accordingly, the present disclosure is not to be considered as limited by the foregoing description.

The invention claimed is:

1. A device comprising:

an inlet port for receiving a fluid flow;

an outlet port in communication with the inlet port;

a collection portion in communication with the inlet port and the outlet port;

a formation portion in communication with the collection portion, wherein the formation portion includes a semi-spherical surface defining a volume for receiving the fluid flow; and a rod configured for insertion into the collection portion and operable to move through the collection portion towards the outlet port, wherein:

the rod is configured to move between a first position proximal to the outlet port and a second position at least partially distal to the outlet port, and the rod is configured to fluidly decouple the collection portion with the outlet port when the rod is in the second position by at least partially blocking the outlet port.

2. The device of claim 1, wherein a central longitudinal axis of the rod is parallel to a central longitudinal axis of the outlet port.

3. The device of claim 1, wherein the formation portion includes a semi-frustoconical surface configured to funnel the fluid flow towards the collection portion.

4. The device of claim 1, wherein the rod is biased toward or away from the outlet port by a resilient element, the rod is configured to move between the first position and the second position when the resilient element moves from a compressed state to an expanded state.

5. The device of claim 4, further comprising a stopper movable between a first position to compress the resilient element into the compressed state, and a second position to release the resilient element into the expanded state.

6. The device of claim 1, further comprising a sheath coupled to, and extending distally from, the outlet port, wherein the rod is operable to guide an amount of material into the sheath, and wherein a distal end of the sheath includes at least one opening configured to distribute the amount of material.

7. The device of claim 6, further comprising a removable plug or cap for the at least one opening of the distal end of the sheath.

8. The device of claim 6, wherein at least the distal end of the sheath includes a hydrophilic coating.

9. The device of claim 4, further comprising a body defining a flow chamber and configured to receive the rod; wherein the rod includes a stopper portion protruding from a radially outer surface of rod, wherein the body includes an offshoot configured to allow the stopper portion to pass through the offshoot, wherein alignment of the stopper portion and the offshoot is configured to cause the resilient member to move from the compressed state to the expanded state.

10. The device of claim 1, wherein the rod is configured to move towards the outlet port along a direction of a material stored in the collection portion upon mixing with the fluid flow.

11. A device comprising:
an inlet port for receiving a fluid flow;
an outlet port in communication with the inlet port;
a collection portion in communication with the inlet port and the outlet port;
a formation portion in communication with the collection portion, the formation portion including a semi-spherical surface and a semi-frustoconical surface opposite from the semi-spherical surface; and
a rod configured for insertion into the collection portion and operable to move through the collection portion towards the outlet port, wherein:
the rod is configured to move between a first position proximal to the outlet port and a second position at least partially distal to the outlet port, and
the rod is configured to fluidly decouple the collection portion with the outlet port when the rod is in the second position by at least partially blocking the outlet port.

12. The device of claim 11, wherein a central longitudinal axis of the rod is parallel to a central longitudinal axis of the outlet port.

13. The device of claim 11, wherein the rod is biased toward or away from the outlet port by a resilient element, the rod is configured to move between the first position and the second position when the resilient element moves from a compressed state to an expanded state.

14. The device of claim 13, further comprising a stopper movable between a first position to compress the resilient element into the compressed state, and a second position to release the resilient element into the expanded state.

15. The device of claim 11, further comprising a sheath coupled to, and extending distally from, the outlet port, wherein the rod is operable to guide an amount of material into the sheath, and wherein a distal end of the sheath includes at least one opening configured to distribute the amount of material.

16. The device of claim 15, further comprising a removable plug or cap for the at least one opening of the distal end of the sheath.

17. The device of claim 15, wherein at least the distal end of the sheath includes a hydrophilic coating.

18. The device of claim 14, wherein the rod includes a stopper portion protruding from a radially outer surface of rod.

19. The device of claim 11, wherein the rod is configured to move towards the outlet port along a direction of a material stored in the collection portion upon mixing with the fluid flow.

* * * * *